US012767690B2

(12) United States Patent
Okada et al.

(10) Patent No.: US 12,767,690 B2
(45) Date of Patent: Oct. 20, 2026

(54) NUCLEIC ACID-BINDING PROTEIN

(71) Applicant: JAPAN SCIENCE AND TECHNOLOGY AGENCY, Saitama (JP)

(72) Inventors: Yasushi Okada, Suita (JP); Daisuke Ino, Suita (JP); Kazuho Ikeda, Tokyo (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 1151 days.

(21) Appl. No.: 17/601,174

(22) PCT Filed: Apr. 9, 2020

(86) PCT No.: PCT/JP2020/015966
§ 371 (c)(1),
(2) Date: Oct. 4, 2021

(87) PCT Pub. No.: WO2020/209332
PCT Pub. Date: Oct. 15, 2020

(65) Prior Publication Data

US 2022/0204569 A1 Jun. 30, 2022

(30) Foreign Application Priority Data

Apr. 9, 2019 (JP) ................................ 2019-074004

(51) Int. Cl.

| | |
|---|---|
| ***C07K 14/195*** | (2006.01) |
| ***A01K 67/0278*** | (2024.01) |
| ***A01K 67/64*** | (2025.01) |
| ***C07K 19/00*** | (2006.01) |
| ***C12N 15/62*** | (2006.01) |
| ***C12N 15/85*** | (2006.01) |
| ***C12N 15/88*** | (2006.01) |
| ***C12Q 1/6876*** | (2018.01) |
| ***G01N 21/64*** | (2006.01) |

(52) U.S. Cl.
CPC ........ *C07K 14/195* (2013.01); *A01K 67/0278* (2013.01); *A01K 67/64* (2025.01); *C07K 19/00* (2013.01); *C12N 15/62* (2013.01); *C12N 15/8509* (2013.01); *C12N 15/88* (2013.01); *C12Q 1/6876* (2013.01); *G01N 21/6402* (2013.01); *G01N 21/6408* (2013.01); *G01N 21/6428* (2013.01); *G01N 21/6456* (2013.01); *A01K 2217/052* (2013.01); *A01K 2227/105* (2013.01); *A01K 2227/703* (2013.01); *A01K 2267/0393* (2013.01); *C12N 2015/859* (2013.01); *C12N 2800/106* (2013.01); *G01N 2021/6439* (2013.01)

(58) Field of Classification Search
CPC .... A01K 67/64; A01K 67/0278; C07K 19/00; C07K 14/195; C12N 15/62; C12N 15/8509; C12N 15/88; C12Q 1/6876; G01N 21/6402; G01N 21/6408; G01N 21/6428; G01N 21/6456
See application file for complete search history.

(56) References Cited

U.S. PATENT DOCUMENTS

2015/0225465 A1 8/2015 Bertonati et al.

FOREIGN PATENT DOCUMENTS

| | | | |
|---|---|---|---|
| CN | 103319574 A | * | 9/2013 |
| CN | 103435691 A | | 12/2013 |
| CN | 104388387 A | | 3/2015 |
| CN | 109384833 A | | 2/2019 |
| JP | 2013-094148 A | | 5/2013 |
| JP | 2013-529083 A | | 7/2013 |
| WO | 2011146121 A1 | | 11/2011 |
| WO | 2014078819 A2 | | 5/2014 |
| WO | 2015020218 A1 | | 2/2015 |
| WO | 2016205554 A1 | | 12/2016 |

OTHER PUBLICATIONS

Fabio C. Rinaldi, Lindsey A. Doyle, Barry L. Stoddard and Adam J. Bogdanove. The effect of increasing numbers of repeats on TAL effector DNA binding specificity, 2017, Nucleic Acids Research, 2017, vol. 45, No. 11 (Year: 2017).*
Lopes Novo C, Rugg-Gunn PJ. Chromatin organization in pluripotent cells: emerging approaches to study and disrupt function. Brief Funct Genomics. 15(4):305-314. doi:10.1093/bfgp/elv029 (Year: 2016).*
Rinaldi FC, Doyle LA, Stoddard BL, Bogdanove AJ. The effect of increasing numbers of repeats on TAL effector DNA binding specificity. Nucleic Acids Res. ; 45(11):6960-6970. doi:10.1093/nar/gkx342. (Year: 2017).*
Shi et al._ Isolated polypeptides and their applications_CN103319574A_ Machine Translation (MT) (Year: 2013).*
Japan Patent Office, "International Search Report for PCT Application No. PCT/JP2020/015966", Japan, Jul. 7, 2020.
Christian, et al., Genetics, 2010, vol. 186, p. 757-761.
(Continued)

*Primary Examiner* — Tracy Vivlemore
*Assistant Examiner* — Kodye Lee Abbott
(74) *Attorney, Agent, or Firm* — Tim Tingkang Xia, Esq.; Troutman Pepper Locke LLP

(57) ABSTRACT

The present invention provides a novel modified protein for detecting a chromatin open structure more sensitively and easily than the prior art as a new detection tool related to gene expression. The present invention relates to a nucleic acid-binding protein comprising a DNA-binding domain in which 3 or more TAL-repeats are repeatedly linked, wherein the nucleic acid-binding protein binds in a base sequence-independent manner, and a method for fluorescently labeling open chromatin in living cells, comprising a step of introducing a gene encoding a nucleic acid-binding protein into a living cell, wherein the nucleic acid-binding protein is a protein in which a DNA-binding domain in which 3 or more TAL-repeats are repeatedly linked and a fluorescent protein are directly or indirectly bound, and the DNA-binding domain binds to a nucleic acid in a base sequence-independent manner.

11 Claims, 8 Drawing Sheets

Specification includes a Sequence Listing.

(56) References Cited

OTHER PUBLICATIONS

Shin-ichi Tate, Significant Role of the Superhelical Motion of TALE in DNARecognition, Biophysics, 2017, vol. 57(3), p. 127-130.
Cermak, et al., Nucleic Acids Research, 2011, vol. 39, e82.
Sakuma et al., Genes to Cells, 2013, vol. 18(4), p. 315-326.
Reyon, et al., "Current Protocols in Molecular Biology", Wiley Online Library, 2012, Chapter 12, 12.15.1-12.15.14.
Chen, et al., Nature Methods, 2016, vol. 13, p. 1013-1020.
Abe et al., Genesis, 2011, vol. 49, p. 579-590.
Derossi, et al., J. Biol. Chem., vol. 269, p. 10444-10450 1994).
Park, et al., Proc. Natl Acad Sci, USA vol. 97, p. 8245-8250 (2000).
Pooga, et al., FASEB J., vol. 12, p. 67-77 (1998).
Oehlke, et al., Biochim Biophys Acta. vol. 1414, p. 127-139 (1998).
Lin, et al., J. Biol. Chem., vol. 270, p. 14255-14258 (1995).
Gao et al, Bioorg. Med. Chem. vol. 10, p. 4057-4065 (2002).
Hong & Clayman, Cancer Res., vol. 60, p. 6551-6556 (2000).
Hongyan Zhou et al., Cell Stem Cell, vol. 4, p. 381-384 (2009).
Dohoon Kim et al., Cell Stem Cell, vol. 4, p. 472-476 (2009).
Takai et al., PNAS, 2015, vol. 112, p. 4352-4356.
Ren, R., et al., "Visualization of aging-associated chromatin alterations with an engineered TALE system.", Cell Research, Jan. 31, 2017, vol. 27, pp. 483-504.
Hu, H., et al., "Live visualization of genomic loci with BiFC-TALE.", Scientific Reports, Jan. 11, 2017, vol. 7, 40192(pp. 1-8).
Ma, H., et al., "Visualization of repetitive DNA sequences in human chromosomes with transcription activator-like effectors.", Proc. Natl. Acad. Sci. USA, Dec. 24, 2013, vol. 110, No. 52, pp. 21048-21053.
Pederson, T., "Repeated TALEs.", Nucleus, Feb. 10, 2014, vol. 5, No. 1, pp. 28-31.
Office Action issued by the State Intellectual Property Office of the Peoples Republic of China for Application No. 202080027140.1, Oct. 18, 2023, China.
Office Action issued by the Japan Patent Office for Application No. 2021-513700, Jun. 28, 2022, Japan.
Gao, H., et al.,"Crystal structure of a TALE protein reveals an extended N-terminal DNA binding region.", Cell Research, Nov. 13, 2012, vol. 22, pp. 1716-1720, DOI: 10.1038/cr.2012.156, [online].
Search Report issued by the European Patent Office for Application No. 20788612.8, Apr. 12, 2023, Europe.
Ting Li et al: "Modularly assembled designer TAL effector nucleases for targeted gene knockout and gene replacement in eukaryotes", Nucleic Acids Research, Oxford University Press, GB, vol. 39, No. 14, Aug. 14, 2011 (Aug. 14, 2011), pp. 6315-6325, XP002680499, ISSN: 1362-4962, DOI:10.1093/NAR/GKR188.
Yang Junjiao et al: "Complete decoding of TAL effectors for DNA recognition", Cell Research, vol. 24, No. 5, Feb. 11, 2014 (Feb. 11, 2014), pp. 628-631, XP93035695, Singapore, ISSN: 1001-0602, DOI: 10.1038/cr.2014.19, Retrieved from the Internet: URL:http://www.nature.com/articles/cr201419>.
Ino Daisukeino et al: "Development of a new fluorescent probe for visualization of open chromatin structure in living cells", WCP2018 (The 18th World Congress of Basic and Clinical Pharmacology), Jul. 2018 (Jul. 2018), XP093035809, Kyoto.
Alan P. Boyle et al: "High-Resolution Mapping and Characterization of Open Chromatin across the Genome", Cell, vol. 132, No. 2, Jan. 2008 (Jan. 2008), pp. 311-322, XP055247811, Amsterdam NL, ISSN: 0092-8674, DOI: 10.1016/j.cell.2007.12.014.

* cited by examiner

SEQUENCE LISTING

```
<160> NUMBER OF SEQ ID NOS: 4

<210> SEQ ID NO 1
<211> LENGTH: 34
<212> TYPE: PRT
<213> ORGANISM: Artificial Sequence
<220> FEATURE:
<223> OTHER INFORMATION: TAL-repeat in which RVD is HT

<400> SEQUENCE: 1
```

Leu Thr Pro Glu Gln Val Val Ala Ile Ala Ser His Thr Gly Gly Lys
1 5 10 15

Gln Ala Leu Glu Thr Val Gln Arg Leu Leu Pro Val Leu Cys Gln Ala
20 25 30

His Gly

<210> SEQ ID NO 2
<211> LENGTH: 34
<212> TYPE: PRT
<213> ORGANISM: Artificial Sequence
<220> FEATURE:
<223> OTHER INFORMATION: TAL-repeat in which RVD is RS

<400> SEQUENCE: 2

Leu Thr Pro Glu Gln Val Val Ala Ile Ala Ser Arg Ser Gly Gly Lys
1 5 10 15

Gln Ala Leu Glu Thr Val Gln Arg Leu Leu Pro Val Leu Cys Gln Ala
20 25 30

His Gly

<210> SEQ ID NO 3
<211> LENGTH: 34
<212> TYPE: PRT
<213> ORGANISM: Artificial Sequence
<220> FEATURE:
<223> OTHER INFORMATION: TAL-repeat in which RVD is HS

<400> SEQUENCE: 3

Leu Thr Pro Glu Gln Val Val Ala Ile Ala Ser His Ser Gly Gly Lys
1 5 10 15

Gln Ala Leu Glu Thr Val Gln Arg Leu Leu Pro Val Leu Cys Gln Ala
20 25 30

His Gly

<210> SEQ ID NO 4
<211> LENGTH: 10617
<212> TYPE: DNA
<213> ORGANISM: Artificial Sequence
<220> FEATURE:
<223> OTHER INFORMATION: Gene coding ChrocodiLE

<400> SEQUENCE: 4
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgcgtaata cgactcacta tagggcgaat tgggtaccac 660
gcgtgtagtc ttatgcaata ctcttgtagt cttgcaacat ggtaacgatg agttagcaac 720

-continued

```
atgccttaca aggagagaaa aagcaccgtg catgccgatt ggtggaagta aggtggtacg    780
atcgtgcctt attaggaagg caacagacgg gtctgacatg gattggacga accactgaat    840
tgccgcattg cagagatatt gtatttaagt gcctagctcg atacaataaa cgggtctctc    900
tggttagacc agatctgagc ctgggagctc tctggctaac tagggaaccc actgcttaag    960
cctcaataaa gcttgccttg agtgcttcaa gtagtgtgtg cccgtctgtt gtgtgactct   1020
ggtaactaga gatccctcag acccttttag tcagtgtgga aaatctctag cagtggcgcc   1080
cgaacaggga cctgaaagcg aaagggaaac cagagctctc tcgacgcagg actcggcttg   1140
ctgaagcgcg cacggcaaga ggcgaggggc ggcgactggt gagtacgcca aaaattttga   1200
ctagcggagg ctagaaggag agagatgggt gcgagagcgt cagtattaag cgggggagaa   1260
ttagatcgcg atgggaaaaa attcggttaa ggccaggggg aaagaaaaaa tataaattaa   1320
aacatatagt atgggcaagc agggagctag aacgattcgc agttaatcct ggcctgttag   1380
aaacatcaga aggctgtaga caaatactgg gacagctaca accatccctt cagacaggat   1440
cagaagaact tagatcatta tataatacag tagcaaccct ctattgtgtg catcaaagga   1500
tagagataaa agacaccaag gaagctttag acaagataga ggaagagcaa aacaaaagta   1560
agaccaccgc acagcaagcg gccgctgatc ttcagacctg gaggaggaga tatgagggac   1620
aattggagaa gtgaattata taaatataaa gtagtaaaaa ttgaaccatt aggagtagca   1680
cccaccaagg caaagagaag agtggtgcag agagaaaaaa gagcagtggg aataggagct   1740
ttgttccttg ggttcttggg agcagcagga agcactatgg gcgcagcctc aatgacgctg   1800
acggtacagg ccagacaatt attgtctggt atagtgcagc agcagaacaa tttgctgagg   1860
gctattgagg cgcaacagca tctgttgcaa ctcacagtct ggggcatcaa gcagctccag   1920
gcaagaatcc tggctgtgga aagataccta aaggatcaac agctcctggg gatttggggt   1980
tgctctggaa aactcatttg caccactgct gtgccttgga atgctagttg gagtaataaa   2040
tctctggaac agattggaat cacacgacct ggatggagtg ggacagagaa attaacaatt   2100
acacaagctt aatacactcc ttaattgaag aatcgcaaaa ccagcaagaa aagaatgaac   2160
aagaattatt ggaattagat aaatgggcaa gtttgtggaa ttggtttaac ataacaaatt   2220
ggctgtggta tataaaatta ttcataatga tagtaggagg cttggtaggt ttaagaatag   2280
tttttgctgt actttctata gtgaatagag ttaggcaggg atattcacca ttatcgtttc   2340
agacccacct cccaaccccg aggggacccg acaggcccga aggaatagaa gaagaaggtg   2400
gagagagaga cagagacaga tccattcgat tagtgaacgg atctcgacgg ttaactttta   2460
aaagaaaagg ggggattggg gggtacagtg caggggaaag aatagtagac ataatagcaa   2520
cagacataca aactaaagaa ttacaaaaac aaattacaaa attcaaaatt ttgggccctt   2580
ccaaccttcc aaccggtacc tagtaatcaa ttacggggtc attagttcat agcccatata   2640
tggagttccg cgttacataa cttacggtaa atggcccgcc tggctgaccg cccaacgacc   2700
cccgcccatt gacgtcaata atgacgtatg ttcccatagt aacgccaata gggactttcc   2760
attgacgtca atgggtggac tatttacggt aaactgccca cttggcagta catcaagtgt   2820
atcatatgcc aagtacgccc cctattgacg tcaatgacgg taaatggccc gcctggcatt   2880
atgcccagta catgacctta tgggactttc ctacttggca gtacatctac gtattagtca   2940
tcgctattac catgggtcga ggtgagcccc acgttctgct tcactctccc catctccccc   3000
ccctccccac ccccaatttt gtatttattt atttttaat tattttgtgc agcgatgggg    3060
gcgggggggg ggggggcgcg cgccaggcgg ggcggggcgg ggcgaggggc ggggcggggc   3120
```

-continued

```
gaggcggaga ggtgcggcgg cagccaatca gagcggcgcg ctccgaaagt ttccttttat   3180
ggcgaggcgg cggcggcggc ggccctataa aaagcgaagc gcgcggcggg cgggagtcgc   3240
tgcgttgcct tcgccccgtg ccccgctccg cgccgcctcg cgccgcccgc cccggctctg   3300
actgaccgcg ttactcccac aggtgagcgg gcgggacggc ccttctcctc cgggctgtaa   3360
ttagcgcttg gtttaatgac ggctcgtttc ttttctgtgg ctgcgtgaaa gccttaaagg   3420
gctccgggag ggccctttgt gcggggggga gcggctcggg gggtgcgtgc gtgtgtgtgt   3480
gcgtggggag cgccgcgtgc ggcccgcgct gcccggcggc tgtgagcgct gcgggcgcgg   3540
cgcggggctt tgtgcgctcc gcgtgtgcgc gaggggagcg cggccggggg cggtgccccg   3600
cggtgcgggg gggctgcgag gggaacaaag gctgcgtgcg gggtgtgtgc gtgggggggt   3660
gagcaggggg tgtgggcgcg gcggtcgggc tgtaaccccc ccctgcaccc ccctccccga   3720
gttgctgagc acggcccggc ttcgggtgcg gggctccgtg cggggcgtgg cgcggggctc   3780
gccgtgccgg gcgggggtg gcggcaggtg ggggtgccgg gcggggcggg gccgcctcgg   3840
gccggggagg gctcggggga ggggcgcggc ggcccccggag cgccggcggc tgtcgaggcg   3900
cggcgagccg cagccattgc cttttatggt aatcgtgcga gagggcgcag ggacttcctt   3960
tgtcccaaat ctggcggagc cgaaatctgg gaggcgccgc cgcacccccct ctagcgggcg   4020
cgggcgaagc ggtgcggcgc cggcaggaag gaaatgggcg gggagggcct tcgtgcgtcg   4080
ccgcgccgcc gtccccttct ccatctccag cctcggggct gccgcagggg gacggctgcc   4140
ttcggggggg acggggcagg gcggggttcg gcttctggcg tgtgaccggc ggctctagag   4200
cctctgctaa ccatgttcat gccttcttct ttttcctaca gctcctgggc aacgtgctgg   4260
ttgttgtgct gtctcatcat tttggcaaag gattcctcga ggtcgacacc atggctccaa   4320
agaagaagcg taaggtagac tacaaagacc atgacggtga ttataaagat catgacatcg   4380
attacaagga tgacgatgac aagggtaccg tggatctgag aaccctgggc tacagccagc   4440
agcagcagga aaagatcaag cccaaagtgc ggagcaccgt ggcccagcac catgaagctc   4500
tcgtgggaca cggcttcacc cacgcccata tcgtggccct gtctcagcat cctgccgccc   4560
tgggaacagt ggccgtgacc taccagcaca tcatcaccgc cctgcctgag gccacccacg   4620
aggatattgt gggagtgggc aagcagtgga gcggcgccag agcactggaa gccctgctga   4680
cagatgccgg cgagctgaga ggacctcccc tgcagctgga tacaggccag ctcgtgaaga   4740
tcgccaagcg gggaggcgtg acagccatgg aagccgtgca cgccagcaga aacgctctga   4800
caggcgctcc cctgaacctg acaccagagc aagtggtggc aatcgcctcc cacactggcg   4860
ggaagcaagc actcgaaact gtccaaaggc ttcttcccgt gctctgccag gctcatgggc   4920
tgacaccaga gcaagtggtg gctattgcat ctcataccgg aggcaaacaa gctctcgaaa   4980
ccgtccagag acttctgcca gtcctctgtc aggctcacgg gctcacacct gaacaggtgg   5040
tcgcaatcgc atctcataca ggaggaaaac aggccctcga aacagtgcaa aggctgctgc   5100
ctgtgctgtg tcaggctcat ggactgacac ctgagcaagt cgtggccatt gcctctcata   5160
caggggggaaa gcaagccctc gaaactgtgc agagactgct tcctgtcctg tgccaggctc   5220
atggacttac acccgaacaa gtggtggcca ttgcatctca taccggaggc aagcaagccc   5280
tcgaaactgt ccagaggctg cttcctgtgc tgtgtcaggc acatggcctt acaccagagc   5340
aggtggtggc tattgcatcc cacactgggg ggaagcaggc tctcgaaact gtccagaggc   5400
ttcttcctgt gctgtgccag gcacatggac tgacacctga acaggtcgtg gctatcgctt   5460
```

-continued

```
ctcatactgg ggggaaacag gctctcgaaa cagtgcagag actgctgcca gtgctttgtc   5520
aagctcatgg ccttacacca gagcaagtcg tcgccatcgc ttctcacact ggcggcaagc   5580
aggccctcga aactgtgcag aggcttcttc ctgtgctttg tcaagctcat ggactgacac   5640
ctgagcaggt cgtcgctatt gcctcccata ctggggggaaa gcaggctctc gaaactgtcc   5700
agaggctcct tcctgtcctt tgtcaagcac atggacttac acccgaacaa gtggtggcca   5760
ttgcatccca taccggcggc aagcaagctc tcgaaaccgt gcaaaggctt cttcccgtgc   5820
tctgccaagc tcatgggctg acacctgaac aggtcgtggc aattgcatcc catactggag   5880
gcaagcaagc actcgaaaca gtgcaaagac tgcttcccgt cctttgtcag gcacacgggc   5940
ttacacctga acaggtggtg gcaattgcct cccataccgg gggaaagcag gctctcgaaa   6000
cagtgcaaag acttctgcct gtgctgtgcc aggcacacgg cctgacaccc gaacaggtgg   6060
tggctatcgc ctcccatacc ggaggcaagc aggctctcga aactgtgcaa agactcctgc   6120
ctgtgctgtg ccaggcacac gggcttacac ctgagcaagt cgtggctatc gcttcccata   6180
cagggggaaa gcaggctctc gaaacagtgc aaaggcttct ccctgtgctt tgtcaggctc   6240
acgggctgac acccgagcaa gtggtcgcca tcgcttctca tacaggcggc aaacaggctc   6300
tcgaaagcat cgtggcccag ctgagcagac ccgaccccgc cctggccgcc ctgaccaacg   6360
accatctggt ggccctggcc tgtctgggag gcagacctgc tatggacgcc gtgaagaagg   6420
gactgcctca cgcccccgag ctgatcagaa gagtgaacag acggatcggc gagcggacca   6480
gccatagagt ggctggatcc atggtgagca agggcgagga gctgttcacc ggggtggtgc   6540
ccatcctggt cgagctggac ggcgacgtaa acggccacaa gttcagcgtg tccggcgagg   6600
gcgagggcga tgccacctac ggcaagctga ccctgaagtt catctgcacc accggcaagc   6660
tgcccgtgcc ctggcccacc ctcgtgacca ccctgaccta cggcgtgcag tgcttcagcc   6720
gctaccccga ccacatgaag cagcacgact tcttcaagtc cgccatgccc gaaggctacg   6780
tccaggagcg caccatcttc ttcaaggacg acggcaacta caagacccgc gccgaggtga   6840
agttcgaggg cgacaccctg gtgaaccgca tcgagctgaa gggcatcgac ttcaaggagg   6900
acggcaacat cctggggcac aagctggagt acaactacaa cagccacaac gtctatatca   6960
tggccgacaa gcagaagaac ggcatcaagg tgaacttcaa gatccgccac aacatcgagg   7020
acggcagcgt gcagctcgcc gaccactacc agcagaacac ccccatcggc gacggccccg   7080
tgctgctgcc cgacaaccac tacctgagca cccagtccgc cctgagcaaa gaccccaacg   7140
agaagcgcga tcacatggtc ctgctggagt tcgtgaccgc cgccgggatc actctcggca   7200
tggacgagct gtacaaggga aagcccatcc ctaacccact gctcggcctg gacagcacct   7260
aacgatccac tagtctcgac tcgacaatca acctctggat tacaaaattt gtgaaagatt   7320
gactggtatt cttaactatg ttgctccttt tacgctatgt ggatacgctg ctttaatgcc   7380
tttgtatcat gctattgctt cccgtatggc tttcattttc tcctccttgt ataaatcctg   7440
gttgctgtct ctttatgagg agttgtggcc cgttgtcagg caacgtggcg tggtgtgcac   7500
tgtgtttgct gacgcaaccc ccactggttg gggcattgcc accacctgtc agctcctttc   7560
cgggactttc gctttccccc tccctattgc cacggcggaa ctcatcgccg cctgccttgc   7620
ccgctgctgg acaggggctc ggctgttggg cactgacaat tccgtggtgt tgtcggggaa   7680
gctgacgtcc tttccatggc tgctcgcctg tgttgccacc tggattctgc gcgggacgtc   7740
cttctgctac gtcccttcgg ccctcaatcc agcggacctt ccttcccgcg gcctgctgcc   7800
ggctctgcgg cctcttccgc atcttcgcct tcgccctcag acgagtcgga tctccctttg   7860
```

ggccgcctcc ccgcctggaa ttaattcgag ctcggtacct ttaagaccaa tgacttacaa 7920
ggcagctgta gatcttagcc actttttaaa agaaaagggg ggactggaag ggctaattca 7980
ctcccaacga aaataagatc tgctttttgc ttgtactggg tctctctggt tagaccagat 8040
ctgagcctgg gagctctctg gctaactagg gaacccactg cttaagcctc aataaagctt 8100
gccttgagtg cttcaagtag tgtgtgcccg tctgttgtgt gactctggta actagagatc 8160
cctcagaccc ttttagtcag tgtggaaaat ctctagcagt agtagttcat gtcatcttat 8220
tattcagtat ttataacttg caaagaaatg aatatcagag agtgagagga acttgtttat 8280
tgcagcttat aatggttaca aataaagcaa tagcatcaca aatttcacaa ataaagcatt 8340
tttttcactg cattctagtt gtggtttgtc caaactcatc aatgtatcta gagcggccgc 8400
caccgcggtg gagctccagc ttttgttccc tttagtgagg gttaattgcg cgcttggcgt 8460
aatcatggtc atagctgttt cctgtgtgaa attgttatcc gctcacaatt ccacacaaca 8520
tacgagccgg aagcataaag tgtaaagcct ggggtgccta atgagtgagc taactcacat 8580
taattgcgtt gcgctcactg cccgctttcc agtcgggaaa cctgtcgtgc cagctgcatt 8640
aatgaatcgg ccaacgcgcg gggagaggcg gtttgcgtat tgggcgctct tccgcttcct 8700
cgctcactga ctcgctgcgc tcggtcgttc ggctgcggcg agcggtatca gctcactcaa 8760
aggcggtaat acggttatcc acagaatcag gggataacgc aggaaagaac atgtgagcaa 8820
aaggccagca aaaggccagg aaccgtaaaa aggccgcgtt gctggcgttt ttccataggc 8880
tccgcccccc tgacgagcat cacaaaaatc gacgctcaag tcagaggtgg cgaaacccga 8940
caggactata aagataccag gcgtttcccc ctggaagctc cctcgtgcgc tctcctgttc 9000
cgaccctgcc gcttaccgga tacctgtccg cctttctccc ttcgggaagc gtggcgcttt 9060
ctcatagctc acgctgtagg tatctcagtt cggtgtaggt cgttcgctcc aagctgggct 9120
gtgtgcacga accccccgtt cagcccgacc gctgcgcctt atccggtaac tatcgtcttg 9180
agtccaaccc ggtaagacac gacttatcgc cactggcagc agccactggt aacaggatta 9240
gcagagcgag gtatgtaggc ggtgctacag agttcttgaa gtggtggcct aactacggct 9300
acactagaag gacagtattt ggtatctgcg ctctgctgaa gccagttacc ttcggaaaaa 9360
gagttggtag ctcttgatcc ggcaaacaaa ccaccgctgg tagcggtggt ttttttgttt 9420
gcaagcagca gattacgcgc agaaaaaaag gatctcaaga agatcctttg atcttttcta 9480
cggggtctga cgctcagtgg aacgaaaact cacgttaagg gattttggtc atgagattat 9540
caaaaaggat cttcacctag atccttttaa attaaaaatg aagttttaaa tcaatctaaa 9600
gtatatatga gtaaacttgg tctgacagtt accaatgctt aatcagtgag gcacctatct 9660
cagcgatctg tctatttcgt tcatccatag ttgcctgact ccccgtcgtg tagataacta 9720
cgatacggga gggcttacca tctggcccca gtgctgcaat gataccgcga gacccacgct 9780
caccggctcc agatttatca gcaataaacc agccagccgg aagggccgag cgcagaagtg 9840
gtcctgcaac tttatccgcc tccatccagt ctattaattg ttgccgggaa gctagagtaa 9900
gtagttcgcc agttaatagt ttgcgcaacg ttgttgccat tgctacaggc atcgtggtgt 9960
cacgctcgtc gtttggtatg gcttcattca gctccggttc ccaacgatca aggcgagtta 10020
catgatcccc catgttgtgc aaaaaagcgg ttagctcctt cggtcctccg atcgttgtca 10080
gaagtaagtt ggccgcagtg ttatcactca tggttatggc agcactgcat aattctctta 10140
ctgtcatgcc atccgtaaga tgcttttctg tgactggtga gtactcaacc aagtcattct 10200

-continued

```
gagaatagtg tatgcggcga ccgagttgct cttgcccggc gtcaatacgg gataataccg  10260

cgccacatag cagaacttta aaagtgctca tcattggaaa acgttcttcg gggcgaaaac  10320

tctcaaggat cttaccgctg ttgagatcca gttcgatgta acccactcgt gcacccaact  10380

gatcttcagc atcttttact ttcaccagcg tttctgggtg agcaaaaaca ggaaggcaaa  10440

atgccgcaaa aaagggaata agggcgacac ggaaatgttg aatactcata ctcttccttt  10500

ttcaatatta ttgaagcatt tatcagggtt attgtctcat gagcggatac atatttgaat  10560

gtatttagaa aaataaacaa ataggggttc cgcgcacatt tccccgaaaa gtgccac     10617
```

NUCLEIC ACID-BINDING PROTEIN

SEQUENCE LISTING

This application includes a Sequence Listing in the ASCII text file in .txt format that is electronically submitted via EFS-Web on Mar. 11, 2022. The ASCII text file contains a sequence listing entitled "1009115115US9_03042022SequenceListing.txt" created on Mar. 4, 2022 and is 14,671 bytes in size. The ASCII text file contains the same sequence as originally filed on Oct. 4, 2021. The Sequence Listing contained in this 1009115115US9_03042022 SequenceListing.txt file is part of the specification and is hereby incorporated by reference herein in its entirety.

CROSS-REFERENCE TO RELATED PATENT APPLICATION

This application claims priority to Japanese Patent Application No. No. 2019-074004 filed on Apr. 9, 2019, the content of which is incorporated herein by reference.

FIELD OF THE INVENTION

The present invention relates to a probe for specifically detecting and visualizing an open chromatin structure in a chromosome with high sensitivity, and a method for labeling the open chromatin in living cells using the probe.

BACKGROUND OF THE INVENTION

In recent years, attention has been focused on the results of epigenome research on the subject of research on the mechanism by which individual cells exert enormous diversity, even though the genomic information that constitutes an individual organism is almost the same. As a result of this progress in epigenome research, it has become clear that it is important to correctly control the maintenance of the expression of genes essential for each cell and the suppression of the expression of unnecessary genes. The cell-specific traits that emerge as a result of these controls are stably maintained across cell division, and this event is called cell memory (or epigenetics).

TAL (Transcription Activator-Like) Effector (TALE) has been identified as a transcription factor involved in gene expression regulation for suppressing the function of the immune system of host cells when infected with pathogenic bacteria (NPL 1). TALE includes in the center thereof a DNA binding domain in which 10 to 30 structural units (module) consisting of about 34 amino acids are linked, the structural unit being called a TAL-repeat (NPL 2). The TAL-repeat consists of two α-helix structures, and has a two-amino acid residue called Repeat Variable Di-residue (RVD) involved in nucleobase recognition in the loop region connecting the two α-helix structures. Each TAL-repeat recognizes one nucleobase according to the amino acid sequence of each RVD.

By linking TAL-repeats having RVDs that specifically recognize a specific nucleobase in an appropriate order, TALE can be modified so as to selectively bind to a nucleic acid containing a specific base sequence. That is, by using a module corresponding to the target DNA sequence in the DNA binding domain of TALE, sequence-dependent binding can be enabled. For example, in genome editing, TALEN (TALE-Nuclease) is used, which is a fusion of TALE and FokI nuclease that are recognized in a nucleic acid sequence-dependent manner (PTL 1).

On the other hand, it is known that organisms have an open chromatin structure in controlling the expression of various genes, for example, their development and differentiation, by partially disaggregating the aggregates consisting of nucleic acids and histones, the aggregates forming a super three-dimensional structure in the nucleus. Analysis of whether or not it has an open chromatin structure is important in the functional analysis of unexplained genes, in particular, such as expression and identification of unknown differentiation-inducing genes involved in specific diseases, expression and identification of unidentified genes involved in carcinogenesis, and further expression and identification of genes involved in metabolic disorders and neurodegeneration based on control mechanisms that have not been elucidated yet.

CITATION LIST

Patent Literature

PTL 1: Japanese Unexamined Patent Application, First Publication No. 2013-529083

Non Patent Literature

NPL 1: Christian, et al., Genetics, 2010, vol. 186, p. 757-761.

NPL 2: Shinichi Tate, biophysics, 2017, Vol 57 (3), p. 127-130.

NPL 3: Cermak, et al., Nucleic Acids Research, 2011, vol. 39, e82.

NPL 4: Sakuma Et al., Genes to Cells, 2013, vol. 18 (4), p. 315-326.

NPL 5: Reyon, et al., "Current Protocols in Molecular Biology", Wiley Online Library, 2012, Chapter 12, 12.15.1-12.15.14

NPL 6: Chen, et al., Nature Methods, 2016, vol. 13, p. 1013-1020.

NPL 7: Abe et al., Genesis, 2011, vol. 49, p. 579-590.

SUMMARY OF THE INVENTION

Technical Problem

The main object of the present invention is to provide a novel modified protein for detecting a chromatin open structure more sensitively and easily than the prior art as a new detection tool related to gene expression.

Solution to Problem

As a result of diligent research, the present inventors have found that in the DNA binding domain of TALE, a TAL-repeat having an RVD consisting of a specific amino acid sequence binds to the four types of nucleobases of adenine, guanine, thymine, and cytosine with almost the same strength, and that a DNA-binding domain in which a TAL-repeat having an RVD that recognizes all four types of nucleobases is repeatedly linked can be a module that strongly binds to a nucleobase in a base sequence-independent manner. Furthermore, the present inventors have found that this DNA-binding domain can be used as a probe for recognizing an open chromatin structure, and thus completed the present invention.

That is, the present invention includes the following (1) to (13).

(1) A nucleic acid-binding protein comprising a DNA-binding domain in which 3 or more TAL-repeats are repeatedly linked, wherein the nucleic acid-binding protein binds to a nucleic acid in a base sequence-independent manner.

(2) The nucleic acid-binding protein according to (1), wherein an RVD sequence of the TAL-repeats is HT, RS, or HS.

(3) The nucleic acid-binding protein according to (1) or (2), wherein a repetition number of the TAL-repeats in the DNA-binding domain is 3 or more and less than 35.

(4) The nucleic acid-binding protein according to any one of (1) to (3), wherein in the DNA binding domain, the TAL-repeats consisting of the same amino acid sequence are linked repeatedly.

(5) The nucleic acid-binding protein according to any one of (1) to (4), wherein the DNA-binding domain is a DNA-binding domain of TALE in which the RVD sequence of the TAL-repeats is modified to HT, RS, or HS.

(6) The nucleic acid-binding protein according to any one of (1) to (5), wherein the TAL-repeats contained in the DNA-binding domain are TAL-repeats of TALE derived from a bacterium belonging to the genus *Xanthomonas*, or TAL-repeats in which an amino acid mutation is introduced in a region other than the RVD of the TAL-repeats.

(7) The nucleic acid-binding protein according to any one of (1) to (6), wherein the protein containing the DNA-binding domain and a fluorescent protein are directly or indirectly bound to each other.

(8) A protein probe comprising the nucleic acid-binding protein according to any one of (1) to (7), which selectively binds to an open chromatin structure.

(9) A nucleic acid molecule containing a base sequence encoding the nucleic acid-binding protein according to any one of (1) to (7).

(10) An expression vector in which the nucleic acid molecule according to (9) is incorporated and capable of expressing the nucleic acid-binding protein according to any one of (1) to (7) in a host cell.

(11) A method for fluorescently labeling open chromatin in living cells, comprising a step of introducing a gene encoding a nucleic acid-binding protein into a living cell, wherein the nucleic acid-binding protein is a protein including a DNA-binding domain in which 3 or more TAL-repeats are repeatedly linked and a fluorescent protein, and the DNA-binding domain binds to a nucleic acid in a base sequence-independent manner.

(12) Transformed cells into which a gene encoding the nucleic acid-binding protein according to any one of (1) to (7) has been introduced, excluding cells constituting humans.

(13) A transformed non-human animal into which a gene encoding the nucleic acid-binding protein according to any one of (1) to (7) has been introduced.

Advantageous Effects of the Invention

The nucleic acid-binding protein according to the present invention strongly binds to a nucleic acid in a base sequence-independent manner. Therefore, it is useful as a probe for recognizing the open chromatin structure of chromosomes.

DETAILED DESCRIPTION OF THE INVENTION

Nucleic Acid-Binding Protein

Figure 1:
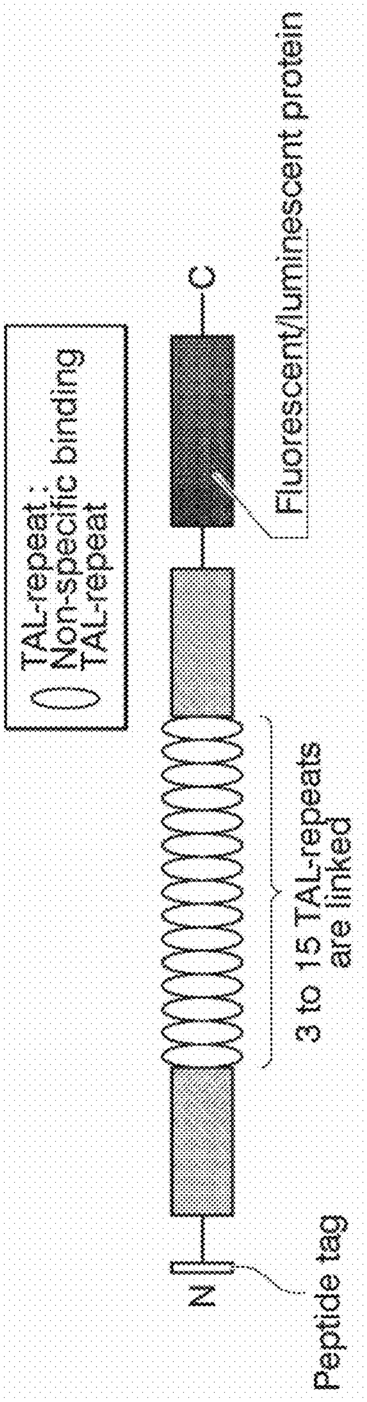
FIG. 1 shows a schematic diagram of the structure of the GFP fusion protein used in Example 1 containing a DNA-binding domain in which TAL-repeats are repeatedly sequenced.

The nucleic acid-binding protein according to the present invention includes a DNA-binding domain in which 3 or more TAL-repeats are repeatedly linked and that binds to a nucleic acid in a base sequence-independent manner. The TAL-repeat in the nucleic acid-binding protein according to the present invention binds to the four types of nucleobases of adenine, guanine, thymine, and cytosine, with almost the same strength. Therefore, the nucleic acid-binding protein according to the present invention having a DNA-binding domain in which the TAL-repeat is repeatedly linked binds strongly to the nucleic acid in a base sequence-independent manner. Hereinafter, the TAL-repeat that binds to the four types of nucleobases with almost the same strength may be referred to as a "non-selective binding TAL-repeat".

The non-selective binding TAL-repeat in the nucleic acid-binding protein according to the present invention is not particularly limited as long as it binds to the four types of nucleobases with almost the same strength. The non-selective binding TAL-repeat preferably has an RVD sequence of HT, RS, or HS (H: histidine, T: threonine, R: arginine, S: serine). TAL-repeats having an RVD consisting of these amino acid sequences bind to the four types of nucleobases to almost the same degree.

RVD of TAL-repeat possessed by a naturally occurring TALE or a variant thereof can be mutated to HT, RS, or HS, and used as the non-selective binding TAL-repeat in the nucleic acid-binding protein according to the present invention. Examples of the naturally occurring TALE include a TALE derived from a *Xanthomonas* bacterium. The *Xanthomonas* bacterium-derived TALE has a DNA-binding domain in which the TAL-repeat is repeatedly sequenced in the center, and has a nuclear localization signal (NLS) sequence and a transcription activation domain on the C-terminal side of the DNA-binding domain (see, for example, NPL 2). The 4th and 32nd amino acids of TAL-repeat of the TALE derived from the *Xanthomonas* bacterium have low storage stability. Examples of the TAL-repeat of natural TALE derived from the *Xanthomonas* bacterium include DD type in which the 4th and 32nd amino acids are both aspartic acid; DA type in which the 4th amino acid is aspartic acid and the 32nd amino acid is alanine; AD type in which the 4th amino acid is alanine and the 32nd amino acid is aspartic acid; AA type in which the 4th amino acid is alanine and the 32nd amino acid is alanine; ED type in which the 4th amino acid is glutamic acid and the 32nd amino acid is aspartic acid; and EA type in which the 4th amino acid is glutamic acid and the 32nd amino acid is alanine. Some natural TALE consist only of the same type of TAL-repeat, and some include 2 or more types of TAL-repeat. For example, some *Xanthomonas* bacteria contain both the DD type TAL-repeat and EA type TAL-repeat in one molecule of TALE.

The variant of TAL-repeat possessed by naturally occurring TALE (TAL-repeat derived from natural TALE) may be a mutant (TAL-repeat mutant) in which a mutation is introduced into 1 or more amino acids, preferably 1 to 10 amino acids, and more preferably 1 to 5 amino acids in a region other than the RVD region in the TAL-repeat while maintaining the function as a TAL-repeat. Mutation means a substitution, deletion or insertion of an amino acid. Examples of the TAL-repeat mutant include mutants having an RVD region consisting of an amino acid sequence having 80% or more sequence identity, preferably 90% or more sequence identity, and more preferably 95% or more sequence identity with the amino acid sequence of the natural TALE-derived TAL-repeat, and that maintains the function as a TAL-repeat. Examples of the naturally occurring variant of TALE include those described in PTL 1. The TAL-repeat with a modified RVD and the TAL-repeat mutant can be manufactured, for example, using a general point mutation introduction technique using a commercially available kit such as KOD-Plus-Mutagenesis Kit (manufactured by Toyobo Co., Ltd.), Prime STAR Mutagenesis Basal Kit (manufactured by Takara), Quik Change Multi Site-Directed Mutagenesis Kit (manufactured by Agilent) or the like.

Examples of the non-selective binding TAL-repeat in the nucleic acid-binding protein according to the present invention include those modified into dipeptides capable of binding RVD of TAL-repeat consisting of 34 amino acids derived from *Xanthomonas* bacterium (12th and 13th amino acids) to four types of nucleobases with almost the same sufficient strength. The amino acid sequences of TAL-repeats in which RVD is modified to HT, RS, or HS are shown in Table 1.

TABLE 1

| RVD | Amino acid sequence | Sequence number |
|---|---|---|
| HT | LTPEQVVAIASHTGGKQALETVQRLLPVLCQAHG | 1 |
| RS | LTPEQVVAIASRSGGKQALETVQRLLPVLCQAHG | 2 |
| HS | LTPEQVVAIASHSGGKQALETVQRLLPVLCQAHG | 3 |

The fourth glutamic acid in the amino acid sequences of SEQ ID NOs: 1 to 3 may be aspartic acid, glutamine, or alanine. Of the amino acid sequences of SEQ ID NOs: 1 to 3, the 32nd alanine may be aspartic acid.

The DNA-binding domain of the nucleic acid-binding protein according to the present invention has a structure in which 3 or more non-selective binding TAL-repeats are repeatedly linked. The higher the repetition number of non-selective binding TAL-repeats in the DNA binding domain, the stronger the binding to the nucleic acid. The repetition number of the non-selective binding TAL-repeats in the nucleic acid-binding protein according to the present invention is preferably 3 or more and less than 35, more preferably 3 to 30, even more preferably 3 to 25, still even more preferably 3 to 25, and particularly preferably 3 to 18. The repetition number of the non-selective binding TAL-repeats in the nucleic acid-binding protein according to the present invention is preferably 8 or more, more preferably 8 or more and less than 35, and even more preferably 10 or more and less than 25. The DNA-binding domain of the nucleic acid-binding protein according to the present invention may consist only of a non-selective binding TAL-repeat consisting of the same amino acid sequence, or may consist of 2 or more types of non-selective binding TAL-repeats consisting of different amino acid sequences. For example, it is allowable that in the plurality of non-selective binding TAL-repeats contained in the DNA binding domain of the nucleic acid binding protein according to the present invention, the amino acid sequences all be the same in the RVD region, but the amino acid sequences in the regions other than the RVD region be different from each other, and it is preferable that 1 to 5 amino acids be different from each other. In addition, it is also allowable that the plurality of non-selective binding TAL-repeats contained in the DNA binding domain of the nucleic acid-binding protein according to the present invention have common amino acid sequences in the regions other than the RVD region, but have amino acid sequences different from each other in the RVD region.

The DNA-binding domain of the nucleic acid-binding protein according to the present invention may include a selective binding TAL-repeat that specifically binds to a specific base as long as the domain as a whole does not interfere with the ability to bind to DNA in a base sequence-independent manner. When a plurality of selective binding TAL-repeats are contained, they may consist of the same amino acid sequence or may consist of 2 or more different amino acid sequences. For example, the DNA binding domain of the nucleic acid-binding protein according to the present invention may include 3 or more non-selective binding TAL-repeats and 1 or more selective binding TAL-repeats. When both non-selective binding TAL-repeat and selective binding TAL-repeat are included, the connection order of these TAL-repeats is not particularly limited, and it is allowable that a block of non-selective binding TAL-repeats and a block of selective binding TAL-repeats be connected, or be alternately connected.

The nucleic acid-binding protein according to the present invention preferably contains an NLS peptide in addition to the above-mentioned DNA-binding domain. By containing an NLS peptide, when the nucleic acid-binding protein according to the present invention is introduced into cells or expressed intracellularly, it can bind to a chromosome in the nucleus of the cell. As the NLS peptide, a known NLS peptide contained in a naturally occurring nuclear-localized protein or a variant thereof can be used.

The nucleic acid-binding protein according to the present invention preferably includes a labeling site for directly or indirectly detecting the presence of the protein. As the labeling site, it can be appropriately selected from those generally used for labeling nucleic acids and proteins such as fluorophores, peptide tags, enzymes, biotin, avidin, streptavidin, colloidal gold, magnetic beads, agarose beads or the like. The fluorescent molecule may be an organic compound other than a protein such as a fluorescein derivative, a rhodamine derivative or the like, or may be a fluorescent protein such as GFP (green fluorescent substance), mTQ2, Citrine, tagRFP, iRFP, mMapple or the like. Examples of the peptide tag include His tag, GST tag, Flag tag, Myc tag, HA tag, tetracystein tag and the like. Examples of the enzyme include HaloTag (haloalkane dehalogenase), SNAP-tag, CLIP-tag (methylguanine DNA methyltransferase), HRP (Horseradish peroxidase), AP (Alkaline phosphatase) and the like.

The nucleic acid-binding protein according to the present invention can be produced, for example, by substituting a DNA-binding domain in naturally occurring TALE or variants thereof (repeating region of TAL-repeat) with a structure in which a non-selective binding TAL-repeat is repeatedly linked 3 or more times. Further, a protein in which a labeling site is directly or indirectly bound to the produced TALE variant via a peptide linker or the like is also included in the nucleic acid-binding protein according to the present invention.

When the nucleic acid-binding protein according to the present invention consists only of a protein, the nucleic acid-binding protein can be produced by using an expression system by introducing an expression vector incorporating a nucleic acid molecule containing a base sequence encoding the full length of the nucleic acid-binding protein into various protein expression systems. When the nucleic acid-binding protein according to the present invention includes a portion other than the protein, such as a non-proteinogenic fluorescent molecule, the nucleic acid-binding protein according to the present invention can be produced by introducing a non-protein molecule into a protein produced by introducing an expression vector incorporating a nucleic acid molecule containing a base sequence encoding only a protein portion containing a DNA-binding domain among the nucleic acid-binding proteins by a conventional method.

Protein Probe

The nucleic acid-binding protein according to the present invention strongly binds to a nucleic acid in a base sequence-independent manner. Therefore, among the nucleic acid-binding proteins according to the present invention, a protein having a labeling site is useful as a protein probe that widely recognizes nucleic acids. In particular, the nucleic acid-binding protein according to the present invention selectively recognizes the open chromatin structure rather than the aggregated chromatin on the chromosome. Therefore, the nucleic acid-binding protein according to the present invention is useful as a probe for recognizing an open chromatin structure. In particular, the nucleic acid-binding protein according to the present invention containing a fluorescent substance as a target site (hereinafter, may be referred to as "nucleic acid-binding fluorescent protein according to the present invention") can be used as a tool for visualizing the open chromatin structure in the living cell in real time. The nucleic acid-binding fluorescent protein according to the present invention can also be used as a tool for visualizing the open chromatin structure in fixed cells.

For example, by expressing or introducing the nucleic acid-binding fluorescent protein according to the present invention into living cells and using it as a probe for visualizing dynamic changes in chromatin, epigenome analysis of the entire cell is made possible. In addition, the nucleic acid-binding fluorescent protein according to the present invention can also be used for analysis of the expression mechanism and differentiation of iPS cells and the like by taking advantage of the fact that the open chromatin structure can be detected in real time. For example, it can be used for cancer treatment to restore tumor tissue to its original differentiated state, or can be used for quality control of artificial cells such as iPS cells. Furthermore, drugs such as steroids are widely distributed in the living body, and they penetrate into the nucleus and regulate the expression state of various genes to exert their effects, and thus it is considered that the nucleic acid-binding fluorescent protein according to the present invention can also be used for kinetics observation of such drugs.

Nucleic Acid Molecule

The nucleic acid molecule containing the base sequence encoding the nucleic acid-binding protein according to the present invention (hereinafter, may be referred to as "nucleic acid molecule according to the present invention") is not particularly limited as long as it is a molecule containing a base sequence from which the amino acid sequence of the target nucleic acid-binding protein can be obtained by translation. Among the nucleic acid molecules according to the present invention, the base sequence encoding the protein portion of the nucleic acid-binding protein according to the present invention is preferably appropriately designed in consideration of the codon use frequency of the host expressing the protein. In order to reduce the risk of homologous recombination, it is also preferable that the base sequences encoding the TAL-repeat portion in the DNA binding domain be designed to be different from each other by utilizing the fluctuation of codons.

The nucleic acid molecule according to the present invention may be obtained by a chemical synthesis based on the base sequence information, or may be obtained by modifying a naturally occurring TALE gene using a conventional technique such as PCR. For example, the nucleic acid molecule according to the present invention can be prepared by using a commercially available kit that can be used for producing a DNA-binding protein using TALE as a DNA-binding domain. As the kit, various kits such as Golden Gate TALEN and TAL Effector Kit based on the Golden Gate method (NPL 3), Yamamoto Lab TALEN Accessory Pack based on the modification method (NPL 4), TALE Toolbox Kit which combines the Golden Gate method and the PCR method, REAL Addgene TALEN Kit based on the REAL method (NPL 5) or the like are available from Addgene. These kits are convenient because conventional TALE fusion proteins can be prepared by simply connecting the modules (DNA binding domains) corresponding to the target DNA sequence according to the manufacturer's manual. When the nucleic acid-binding protein according to the present invention does not contain a nuclease, the FokI functional domain may be simply removed from the vectors included in these kits. Further, the nucleic acid molecule according to the present invention can also be obtained by appropriately introducing a mutation into the vector of the above kit by using the general point mutation introduction technique mentioned above or a conventional technique such as PCR. In addition, the nucleic acid molecule according to the present invention can also be produced by total synthesis using artificial gene synthesis technology.

Expression Vector

The expression vector according to the present invention is an expression vector in which a nucleic acid molecule according to the present invention is incorporated and that can express a nucleic acid-binding protein according to the present invention in host cells. Specifically, from the upstream, an expression cassette composed of a DNA having a promoter sequence, a nucleic acid molecule according to the present invention, and a DNA having a terminator sequence is incorporated into an expression vector. The expression cassette can be prepared and incorporated into an expression vector by using a well-known gene recombination technique. A commercially available expression vector preparation kit may be used for incorporation of the polynucleotide into the expression vector.

The host cells may be prokaryotic cells or eukaryotic cells. As the prokaryotic cells, a bacterium belonging to the genus *Escherichia* such as *Escherichia coli* or the like; a bacterium belonging to the genus *Bacillus* such as *Bacillus subtilis* or the like; an *agrobacterium* belonging to the genus *Rhizobium* (for example, *Rhizobium tumefaciens, Rhizobium rhizogenes*) or the like; and the like can be used. As the eukaryotic cells, yeasts such as *Saccharomyces cerevisiae, Schizosaccharomyces pombe* or the like; insect cells such as *Spodoptera frugiperda* cells (Sf cells) derived from larvae of *Spodoptera frugiperda* or the like; animal cells; plant cells; and the like can be used. Examples of the animal cells include established cultured cells such as HEK293 cells (human-derived culture line), COS-7 cells (monkey-derived culture line), CHO cells (Chinese hamster-derived culture line) or the like; primary cultured cells collected from fetal or adult tissues such as mouse fetal fibroblast MEF and primary cultured neurons or the like; ES cells created from fertilized eggs; iPS cells established from primary cultured cells; and the like. Examples of the plant cells include cells in the plant body as well as the cultured cells derived from plants. In addition, various forms of plant-derived plant cells such as suspension-cultured cells, protoplasts, leaf sections, callus, immature embryos, pollen and the like are included.

The animal cells used as host cells may be cells derived from a mammal or cells derived from an animal other than a mammal. Examples of the mammals include rodents such as mice, rats, hamsters, guinea pigs or the like, and experimental animals such as rabbits or the like; livestock such as pigs, cows, goats, horses, sheep, mink or the like; pets such as dogs, cats or the like; human or non-human primates (e.g., monkeys, cynomolgus monkeys, rhesus monkeys, marmosets, orangutans, chimpanzees, etc.), and the like. In addition, examples of the animals other than mammals include, but are not limited to, experimental animals such as nematodes (*C. elegans*), insects (*Drosophila*), fish (zebrafish, killifish), amphibians (*Xenopus laevis, Xenopus laevis*) and the like.

The plant cells used as host cells are not particularly limited as long as the cells are other than animal cells, in other words, cells having a cell wall, and examples thereof include cells derived from any plant such as angiosperms and nude plants (seed plants) including monocotyledonous and dicotyledonous plants, moss plants, fern plants, herbaceous plants, wood plants or the like, and the like. Specific examples of the plants include solanaceae plants such as eggplants, tomatoes, peppers, capsicums, tobacco or the like; gramineae plants such as rice, wheat, barley, perennial ryegrass, Italian ryegrass, meadow fescue, tall fescue, orchard grass, timothy or the like; cruciferous plants such as *Arabidopsis thaliana*, oilseed rape, Chinese cabbage, cabbage, radish, rapeseed or the like; legumes such as soybeans, adzuki beans, green beans, broad beans or the like; cucurbitaceae plants such as cucumbers, melons, watermelons, pumpkins or the like; convolvulaceae plants such as sweet potatoes or the like; liliaceae plants such as leeks, onions, garlic, garlic, asparagus or the like; labiatae plants such as perilla or the like; asteraceae plants such as chrysanthemum, garland chrysanthemum, lettuce or the like; rosaceae plants such as roses, strawberries or the like; rutaceae plants such as mandarin oranges, Japanese pepper or the like; myrtaceae plants such as eucalyptus or the like; willow family plants such as poplar or the like; chenopodiaceae plants such as spinach, sugar beet or the like; gentianaceae plants such as gentian or the like; dianthus plants such as carnations or the like; and the like. In particular, solanaceae plants and cruciferous plants are preferable, and tomatoes, tobacco and *Arabidopsis thaliana* are particularly preferable.

Examples of the type of the expression vector include a plasmid vector, a viral vector and the like, and the expression vectors may be appropriately selected depending on the host cells to be used. The expression vector according to the present invention can be produced by functionally linking the nucleic acid according to the present invention downstream of a promoter in an appropriate expression vector. The expression vector according to the present invention to be introduced into host cells is preferably isolated or purified.

Examples of the plasmid vector include plasmid vectors derived from *Escherichia coli* such as pBR322, pBR325, pUC12, pUC13 or the like; plasmid vectors derived from *Bacillus subtilis* such as pUB110, pTP5, pC194 or the like; plasmid vectors derived from yeast such as pSH19, pSH15 or the like; plasmid vectors for eukaryotic cells such as pCS2, pCMV, pcDNA, pCAGGS or the like; binary vectors for plant cells, and the like. The plasmid vectors may be appropriately selected according to the type of host cells to be used and the purpose of use.

When the expression vector according to the present invention is a viral vector, the type of viral vector to be used can be appropriately selected according to the type of the host cell to be used and the purpose of use. For example, when insect cells are used as the host, a baculovirus vector or the like can be used. When mammalian cells are used as the host, retrovirus vectors such as Moloney mouse leukemia virus vector, lentivirus vector, Sindbis virus vector or the like, adenovirus vector, herpesvirus vector, adeno-associated virus vector, parvovirus vector, waxinia virus vector, sendai virus vector, and the like can be used.

Further, as the promoter used in the expression vector according to the present invention, a promoter capable of initiating transcription in the host cells can be selected according to the type of host cell used. For example, when the host is genus *Escherichia*, trp promoter, lac promoter, T7 promoter and the like are preferable. When the host is genus *Bacillus*, SPO1 promoter, SPO2 promoter, penP promoter and the like are preferable. When the host is yeast, PHO5 promoter, PGK promoter and the like are preferable. When the host is insect cells, a polyhedrin promoter, a P10 promoter and the like are preferable. When the host is mammalian cells, a subgenomic (26S) promoter, a CMV promoter, an SR$\alpha$ promoter, a CAG promoter, an EF1 promoter and the like are preferable.

If desired, the expression vector according to the present invention may contain an enhancer, a splicing signal, a poly A addition signal, a selectable marker, an SV40 origin of replication, and the like in a functional manner. Examples of the selectable marker include a dihydrofolate reductase gene [methotrexate (MTX)-resistant gene], an ampicillin-resistant gene, a neomycin-resistant gene, a kanamycin-resistant gene, a hygromycin-resistant gene and the like.

By introducing the expression vector according to the present invention into the host cells according to a known gene transfer method, a transformant (transformed cells) into which the expression vector is introduced can be produced. Examples of the known gene transfer methods include a lipofection method, a calcium phosphate method, a microinjection method, a protoplast fusion method, an electroporation method, a DEAE dextran method, a gene transfer method using Gene Gun, and the like. The prepared transformant can express the nucleic acid-binding protein according to the present invention. That is, the expression vector according to the present invention and the transformant into which the expression vector is introduced are useful for the production of the nucleic acid-binding protein according to the present invention.

By synthesizing an RNA from the expression vector according to the present invention by an in vitro transcription reaction and introducing it into a fertilized egg or cells, the nucleic acid-binding protein according to the present invention can be expressed intracellularly. The nucleic acid-binding protein according to the present invention can be produced by culturing the transformed cells into which the expression vector according to the present invention is introduced by a known method according to the type of the host. The produced nucleic acid-binding protein may be used as it is in the transformed cells, or may be isolated or purified from the culture of the transformed cells.

Culturing of the transformed cells whose host is a bacterium belonging to the genus *Escherichia* is usually carried out in a suitable medium such as LB medium, M9 medium or the like at about 15 to 43° C. for about 3 to 24 hours. Culturing of the transformed cells whose host is a bacterium belonging to the genus *Bacillus* is usually carried out in a suitable medium at about 30 to 40° C. for about 6 to 24 hours. Culturing of the transformed cells whose host is a yeast is usually carried out in a suitable medium such as Burke Holder medium or the like at about 20 to 35° C. for about 24 to 72 hours. Culturing of the transformed cells whose host is insect cells or an insect is usually carried out in a suitable medium such as Grace's Insect medium supplemented with about 10% bovine serum, or the like, at about 27° C. for about 3 to 5 days. Culturing of the transformed cells whose host is animal cells is usually carried out at about 30 to 40° C. for about 15 to 60 hours in a suitable medium such as MEM medium supplemented with about 10% bovine serum, or the like. In any of the cultures, aeration and stirring may be performed as needed. Isolation or purification of the nucleic acid-binding protein according to the present invention from a culture can be achieved by subjecting the cell lysate or culture supernatant to a plurality of chromatographies such as reverse phase chromatography, ion exchange chromatography, affinity chromatography or the like.

By introducing the expression vector according to the present invention into a fertilized egg of a non-human animal according to a known gene transfer method, the nucleic acid molecule according to the present invention is incorporated into the cells constituting the body, and a transformed non-human animal expressing the nucleic acid-binding protein according to the present invention can be obtained constantly or under a specific condition. The nucleic acid molecule according to the present invention may be integrated intrachromosomally or extrachromosomally. Further, when the nucleic acid molecule according to the present invention contains a promoter of a gene that is expressed in a tissue-specific manner, a transformed non-human animal in which the nucleic acid-binding protein according to the present invention is expressed only in the specific tissue can be obtained. The expression vector can be introduced into a fertilized egg by using a known method such as a microinjection method. As the fertilized egg into which the expression vector according to the present invention is introduced, fertilized eggs derived from animals other than humans among the animals listed as the origin of the animal cells used as host cells can be used.

By introducing the expression vector according to the present invention into plant callus according to a known gene transfer method and redifferentiating the obtained transformed callus, a redifferentiated individual of a transformed plant in which the nucleic acid-binding protein according to the present invention is expressed in the cells can be obtained. The expression vector can be introduced into the callus by using a known method such as the *Agrobacterium* method. As the callus into which the expression vector according to the present invention is introduced, a callus prepared by a conventional method from a plant listed as the origin of plant cells used as host cells can be used.

The transformed animals and plants expressing the nucleic acid-binding protein according to the present invention, or tissues and cells collected therefrom, are useful as a tool for analyzing the open chromatin structure. For example, the transformed animal or the transformed plant expressing the nucleic acid-binding fluorescent protein according to the present invention can visualize the open chromatin structure in real time, and therefore, the change in the open chromatin structure due to the drug treatment can be observed by analyzing the open chromatin structure at a specific developmental/differentiation stage or by examining the open chromatin structure before and after a specific drug treatment.

For example, by expressing or introducing the nucleic acid-binding fluorescent protein according to the present invention into living cells and using it as a probe for visualizing dynamic changes in chromatin, epigenome analysis of the entire cell is made possible. In addition, the nucleic acid-binding fluorescent protein according to the present invention can also be used for analysis of the expression mechanism and differentiation of iPS cells and the like by taking advantage of the fact that the open chromatin structure can be detected in real time.

Method of Fluorescently Labeling Open Chromatin in Living Cells

By introducing the nucleic acid-binding fluorescent protein according to the present invention into living cells, the open chromatin structure can be fluorescently labeled. When the nucleic acid-binding fluorescent protein according to the present invention is a protein containing a DNA-binding domain having a structure in which 3 or more, more preferably 8 or more non-selective binding TAL-repeats are repeatedly linked and a fluorescent protein, the nucleic acid molecule (gene) encoding the protein can be introduced into the living cells and the protein can be expressed in the living cells. As the living cells to be introduced, the same cells as those mentioned in the above-mentioned method for producing a transformant can be used. In addition, the method for introducing a gene (nucleic acid molecule) into living cells can be carried out in the same manner as the method for producing a transformant described above.

The nucleic acid-binding fluorescent protein according to the present invention may be purified and directly injected into living cells.

The introduction of the nucleic acid-binding fluorescent protein according to the present invention into living cells can be carried out by using a known method for introducing a protein into the cells. Examples of the method include a method using a protein transfer reagent, a method using a protein transfer domain (PTD) or a cell-penetrating peptide (CPP) fusion protein, an electroporation method, a microporation method, a microinjection method, delivery by a bacterial type III secretion system and the like. As the protein introduction reagent, BioPOTER Protein Delivery Reagent (manufactured by Gene Therapy Systems), Pro-Ject (registered trademark) Protein Transfection Reagent (manufactured by PIERCE) and Projectin (manufactured by IMGENEX) based on cationic lipids, Profect-1 (Targeting Systems) based on lipids, Penetrain Peptide (manufactured by Q biogene) and Chariot Kit (manufactured by Active Motif) based on membrane-permeable peptides, Genom ONE (manufactured by Ishihara Sangyo Co., Ltd.) using an HVJ envelope (inactivated Sendai virus), and the like are commercially available. Although the introduction can be performed according to the protocol attached to these reagents, the general procedure is as follows. The nucleic acid-binding fluorescent protein according to the present invention is diluted with a suitable solvent (for example, a buffer solution of PBS, HEPES, etc.), and then an introduction reagent is added thereto, followed by incubating at room temperature for about 5 to 15 minutes to form a complex. The resulting complex is added to cells placed in a serum-free medium and incubated at 37° C. for 1 to several hours. Then, the medium is removed and replaced with a serum-containing medium. For the introduction of proteins into plant cells, protoplasts can also be prepared from the cells according to known methods.

As the PTD, those using the cell transit domain of a protein such as AntP derived from *Drosophila*, TAT (Frankel, et al., Cell, vol. 55, p. 1189-1193 (1988); Green & Loewenstein, Cell, vol. 55, p. 1179-1188 (1988)), Penetratin (Derossi, et al., J. Biol. Chem., vol. 269, p. 10444-10450 (1994); Park, et al., Proc. Natl Acad Sci, USA vol. 97, p. 8245-8250 (2000)), Transportan (Pooga, et al., FASEB J., vol. 12, p. 67-77 (1998)), MAP (model amphipathic peptide) (Oehlke, et al, Biochim Biophys Acta. Vol. 1414, p. 127-139 (1998)), K-FGF (Lin, et al., J. Biol. Chem., vol. 270, p. 14255-14258 (1995)), Ku70 (Sawada, et al., Nature Cell Biol. Vol. 5, p. 352-357 (2003)), Prion (Lundberg, et al., Biochem. Biophys. Res. Commun. Vol. 299, p. 85-90 (2002)), pVEC (Elmquist, et al., Exp. Cell Res., vol. 269, p. 237-244 (2001)), Pep-1 (Morris, et al., Nature Biotechnol. Vol. 19, p. 1173-1176 (2001)), Pep-7 (Gao et al, Bioorg. Med. Chem. Vol. 10, p. 4057-4065 (2001)), SynBl (Rousselle, et al., Mol. Pharmacol. Vol. 57, p. 679-686(2000)), HN-I (Hong & Clayman, Cancer Res., vol. 60, p. 6551-6556 (2000)) derived from HIV, VP22 derived from HSV, or the like have been developed. Examples of CPP derived from PTD include polyarginines such as 11R (Cell Stem Cell, vol. 4, p. 381-384 (2009)) and 9R (Cell Stem Cell, vol. 4, p. 472-476 (2009)) and the like.

A fusion protein expression vector incorporating the cDNA of the nucleic acid-binding fluorescent protein according to the present invention and a PTD sequence or CPP sequence is prepared and recombinantly expressed, and the fusion protein is recovered and used for introduction. The introduction can be carried out in the same manner as described above except that the protein introduction reagent is not added.

Microinjection is a method in which a protein solution is put into a glass needle having a tip diameter of about 1 μm and the cells are punctured to reliably introduce the protein into the cells.

In addition, protein introduction methods such as electroporation methods, semi-intact cell method (Kano, et al., Methods in Molecular Biology, vol. 322, p. 357-365 (2006)), an introduction method using Wr-T peptide (Kondo, et al., Mol. Cancer Ther. Vol. 3 (12), p. 1623-1630 (2004)), or the like can also be used.

The protein introduction operation can be performed any number of times, for example, once or more and 10 times or less, preferably twice or more, more preferably twice or more and 5 times or less, and even more preferably 3 or 4 times. The interval between repeating the introduction operation can be, for example, 6 to 48 hours, and preferably 12 to 24 hours.

EXAMPLES

Next, the present invention will be described in more detail with reference to Examples and the like, but the present invention is not limited to these Examples.

Example 1

The RVD sequence was examined for the DNA-binding domain of about 1,000 types of TALE possessed by various bacteria of the genus *Xanthomonas*, and the TALE variant containing the TAL-repeats containing these RVD sequences was prepared and the bonding property to a nucleobase was examined.

Production of Protein with DNA Binding Domain

TAL-repeats with various RVD sequences were prepared by PCR based on the TALE sequences of known *Xanthomonas* bacterium. By repeatedly linking the obtained TAL-repeats, a protein having a DNA-binding domain in which 15 TAL-repeats having the desired RVD sequence were repeatedly sequenced were prepared. The protein also has a peptide tag at the N-terminal and has a fluorescent protein (EGFP, etc.) or a photoprotein (cyan Nano-Lantern, etc.) at the C-terminal (Takai et al., PNAS, 2015, vol. 112, p. 4352-4356).

A schematic diagram of the structure of the GFP fusion protein used as the visualization probe is shown in FIG. 1. The GFP fusion protein has a DNA-binding domain in which TAL-repeats are repeatedly sequenced, and has a peptide tag at the N-terminal and a GFP protein at the C-terminal.

Evaluation of Nucleic Acid Binding Specificity

The binding property of the prepared TALE variant to the nucleobase was measured by a reporter assay method using the intracellular photoprotein orange Nano-Lantern (Takai et al., Ibid) and the ELISA method in vitro. In the ELISA method, a photoprotein fused to the C-terminal of each protein was used.

As a result, as the TALE variant that binds to the four base residues with an approximately equal binding force, a variant was selected consisting of the amino acid sequences of SEQ ID NOs: 1 to 3, that is, the amino acid sequences whose RVD sequences are HT, RS, or HS, and the amino acid sequences whose 4th and 32nd amino acid sequences are glutamic acid and alanine, respectively.

Effect of TAL-Repeat Repetition Number on Binding to Open Chromatin Structure

A DNA-binding domain consisting of TAL-repeats that non-selectively bind to four types of bases was introduced into living cells as an EGFP fusion protein, and whether or not the domain can be used as a probe for recognizing an open chromatin structure was investigated. At this time, DNA-binding domains having different numbers of TAL-repeat repetitions were introduced, and the effect of the difference in TAL-repeat repetition number on binding to the open chromatin structure was investigated.

As the DNA binding domain, one having a structure in which 1 or 2, 3, 8, 12, or 15 non-selective binding TAL-repeats (RVD sequence is HT) consisting of the amino acid sequence of SEQ ID NO: 1 were repeatedly linked was used. In addition, the expression vector incorporating a nucleic acid molecule encoding the GFP fusion protein having each DNA-binding domain was prepared using the kit as described above.

The cells expressing the GFP fusion proteins with different numbers of non-selective binding TAL-repeat repeats in the DNA binding domain were subjected to fluorescence recovery after photobleaching (FRAP), and the binding activity between DNA and the GFP fusion protein was examined. Specifically, the prepared expression vector was introduced into HeLa cells using a lipofection reagent to express the GFP fusion protein.

Figure 2A:
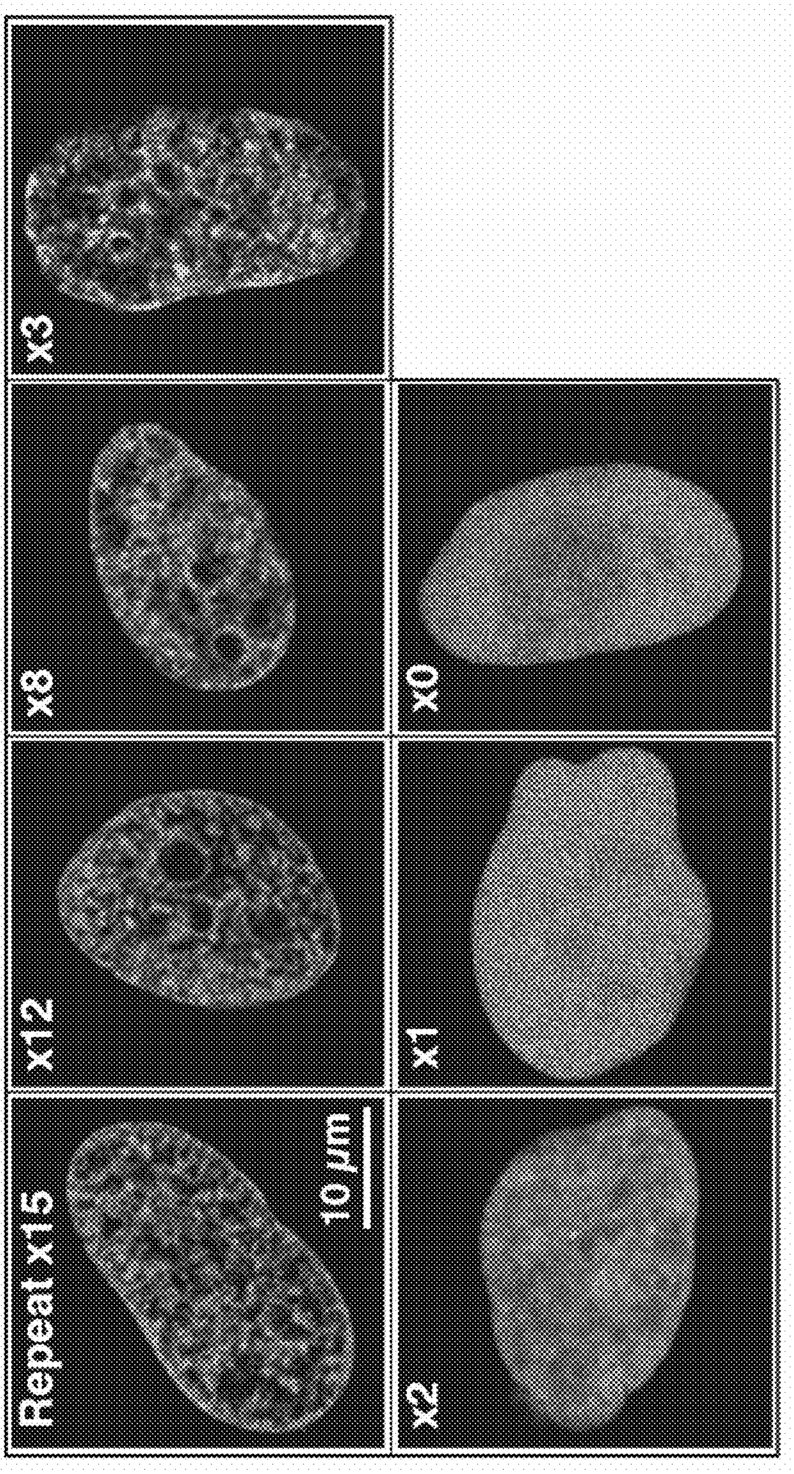
FIG. 2A shows a fluorescence image of cells expressing each GFP fusion protein in Example 1.

A fluorescence image of the cells expressing the GFP fusion protein is shown in FIG. 2A. Table 2 shows the results of the non-uniformity tendency (coefficient of variation) of nuclear staining. As a result, the GFP fusion protein in which the repetition number of non-selective binding TAL-repeats of the DNA-binding domain is one or two was localized in the nucleus in a nearly uniform state, and there was no difference in localization compared to the GFP fusion protein that did not contain the non-selective binding TAL-repeat. In contrast, in the GFP fusion protein having a DNA-binding domain in which the repetition number of non-selective binding TAL-repeats is 3 or more, a fluorescent image that appears to be bound to a specific genomic structure in the nucleus was obtained.

Figure 2B:
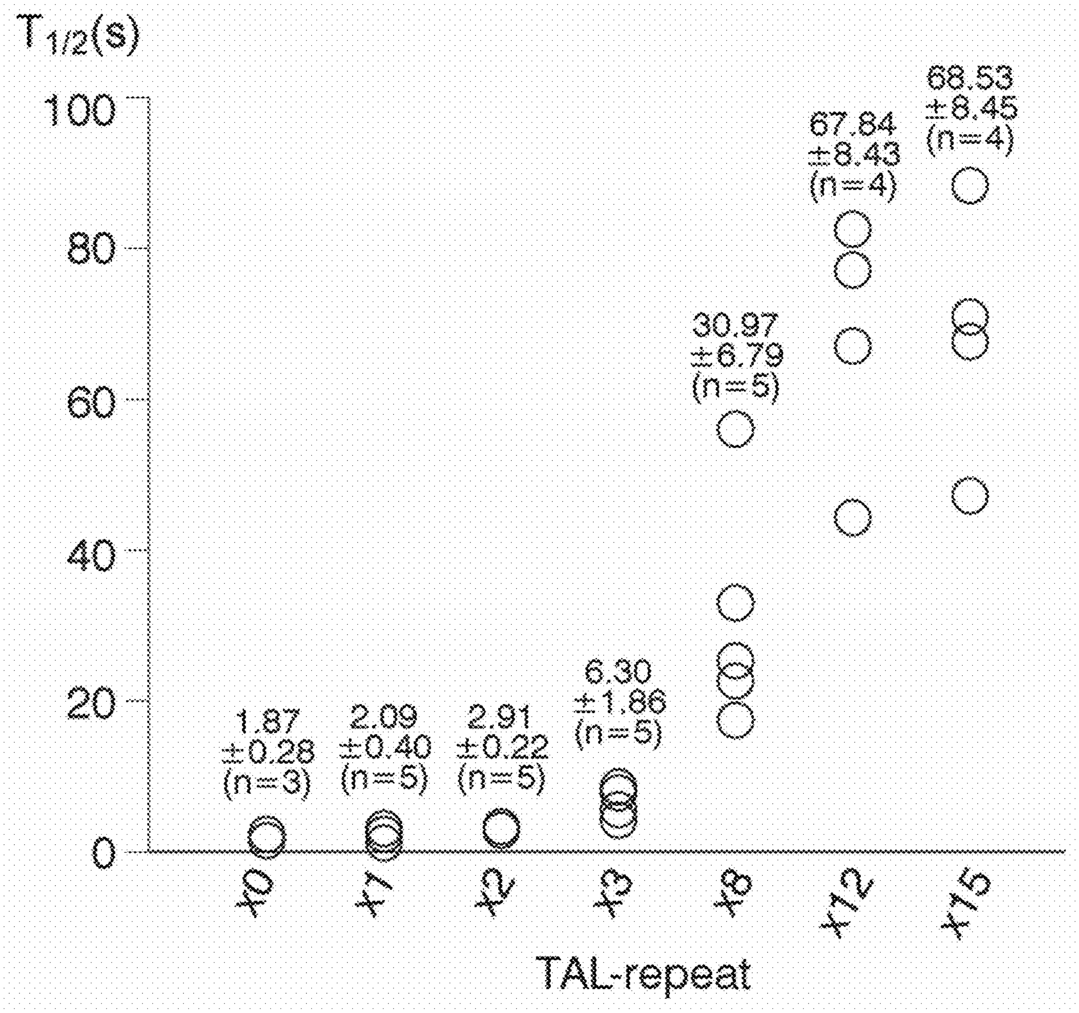
FIG. 2B shows a diagram showing the measurement results of FRAP of each GFP fusion protein in Example 1.

The nuclei of the expressed cells were irradiated with laser light, and the time required for the fluorescence of the region faded by the laser light to recover was measured. The measurement results of FRAP are shown in Table 2 and FIG. 2B. In the GFP fusion protein having a DNA-binding domain in which the repetition number of non-selective binding TAL-repeats was 3 or more, the time required for fluorescence recovery in FRAP ($T_{1/2}$) was significantly longer, and when the repetition number was 8 or more, the time required for recovery was clearly extended. Furthermore, when the repetition number was 12 and 15, and the TAL-repeats were repeated in tandem, a significant increase in the time required for recovery was observed. On the other hand, the non-uniformity of nuclear staining was almost the same to that of the cells without non-selective binding TAL-repeats when the repetition number of non-selective binding TAL-repeats is 1 or 2, and increased greatly when the repetition number was 3 or more. However, the non-uniformity of nuclear staining was almost the same when the repetition number was 3 to 15. From these results, it was confirmed that the DNA-binding domain having 3 or more repeats of the non-selective binding TAL-repeat can bind to the nucleic acid in the chromosome, that as the repetition number increases, the binding force to nucleic acid increases, and that the specificity of the binding to nucleic acid is almost saturated with a repetition number of 3, and does not change much even if the repetition number is increased to 15.

TABLE 2

| Repetition number of non-selective binding TAL-repeats | $T_{1/2}$ [s] | Non-uniformity of nuclear staining (coefficient of variation) |
|---|---|---|
| 0 | 1.87 ± 0.28 (n = 3) | 0.53 |
| 1 | 2.09 ± 0.40 (n = 5) | 0.45 |
| 2 | 2.91 ± 0.22 (n = 5) | 0.40 |
| 3 | 6.30 ± 1.86 (n = 5) | 1.2 |
| 8 | 30.97 ± 6.79 (n = 5) | 0.87 |
| 12 | 67.84 ± 8.43 (n = 4) | 1.1 |
| 15 | 68.53 ± 8.45 (n = 4) | 1.1 |

Example 2

In order to investigate which structure in the nucleus is labeled by a DNA-binding domain in which multiple non-selective binding TAL-repeats are repeatedly sequenced, it was compared with the labeling methods used to label various genomic structures in conventional epigenome analysis. As the conventional labeling method, nuclear staining, a method of immunostaining various modified histones, and the ATAC-see method (NPL 6) were used.

As the fluorescent protein containing the DNA binding domain, the GFP fusion protein with a DNA-binding domain in which 15 non-selective binding TAL-repeats are repeatedly linked, which was prepared in Example 1 (hereinafter, may be referred to as "ChrocodiLE"), was used.

First, live HeLa cells expressing ChrocodiLE were stained with Hoechst (SiR-Hoechst) fused with silicon rhodamine, and the intracellular localization of ChrocodiLE and SiR-Hoechst was compared. Further, a ChrocodiLE expression vector was introduced into HeLa cells that stably express the red fluorescent protein (RFP)-fused histone 2B (H2B) protein, and both were co-expressed to compare the intracellular localization of Chrocode LE and H2B in live cells. As a result, the sites that were heavily stained with SiR-Hoechst, reflecting the local density of nucleosomes, and the heterochromatin accumulation sites around the nuclear envelope and the nucleolus, which were heavily stained with FRB-H2B, were hardly stained with ChrocodiLE. From these results, it was confirmed in living cells that ChrocodiLE did not bind to the heterochromatin concentration site or the heterochromatin accumulation site.

Next, HeLa cells expressing ChrocodiLE were immobilized, and the genome (open chromatin) accessible to the transposase was labeled with a red fluorescent substance by the ATAC (Assay for Transposase-Accessible Chromatin)—see method (in situ hybridization using fluorescently labeled Tn5 transposase).

Independently, HeLa cells expressing ChrocodiLE were immobilized, and each modified histone was fluorescently immunostained using an anti-H3K4me3 antibody, an anti-H3K27ac antibody, an anti-H3K9me3 antibody, or an anti-H3K27me3 antibody as the primary antibody, and using an antibody labeled with a red fluorescent substance as a secondary antibody. H3K4me3 and H3K27ac are modified types of histones mainly present in open chromatin, and H3K9me3 and H3K27me3 are modified types of histones mainly present in aggregated chromatin.

Figure 3A:
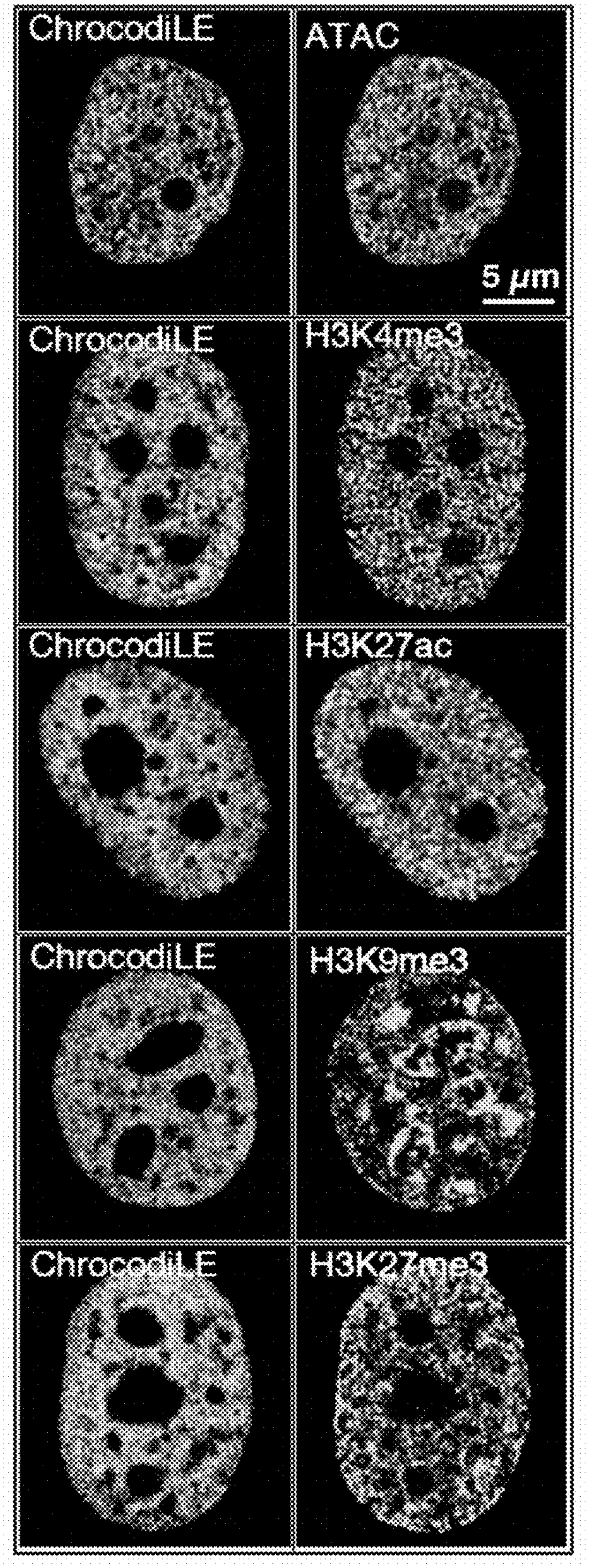
FIG. 3A shows a fluorescence image obtained by double staining of ChrocodiLE (GFP fusion protein containing a DNA-binding domain in which 15 TAL-repeats prepared in Example 1 are repeatedly sequenced), and fluorescently labeled staining (ATAC) with transposases inserted into accessible genomic regions or fluorescent immunostaining against four modified histones (H3K4me3, H3K27ac, H3K9me3, or H3K27me3) in Example 2.
Figure 3B:
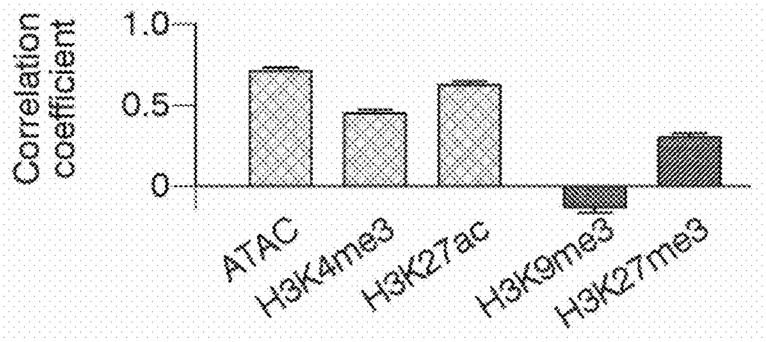
FIG. 3B shows the results of examining the correlation coefficient of co-localization between ChrocodiLE and a genome accessible to four modified histones or transposases in Example 2.

The fluorescence image of each cell after fluorescence staining is shown in FIG. 3A. In addition, the ratio (correlation coefficient) of the green fluorescence of Chrocode LE co-localized with the red fluorescence was examined for each cell after fluorescence staining. The results are shown in FIG. 3B. As a result, ChrocodiLE had a high correlation coefficient with ATAC, H3K4me3 and H3K27ac, and in particular, the correlation coefficient with ATAC was as high as 0.5 or more. On the other hand, ChrocodiLE had a low correlation coefficient with H3K9me3 and H3K27me3, and in particular, was not co-localized with H3K9me3. From these results, it was shown that ChrocodiLE specifically recognizes the open chromatin structure.

The chromatin immunoprecipitation (ChIP) method and the DNA sequencing method using a next-generation sequencer were then used to examine the ChrocodiLE binding region in the genome. Specifically, HeLa cells expressing ChrocodiLE were fixed with formaldehyde to cross-link genomic DNA and ChrocodiLE, and then the genomic DNA was recovered and fragmented by enzymatic digestion. The shredded genomic DNA was immunoprecipitated using an antibody against the N-terminal peptide tag of ChrocodiLE, and the base sequence of the recovered DNA was analyzed using a next-generation sequencer. As a result, the nucleotide sequence of the genomic region to which ChrocodiLE was bound was identified.

HeLa cells not expressing ChrocodiLE were also subjected to ChIP using an anti-H3K4me3 antibody, an anti-H3K27ac antibody, an anti-H3K9me3 antibody, or an anti-H3K27me3 antibody, the base sequence of the DNA recovered by immunoprecipitation was analyzed with a next-generation sequencer, and the nucleotide sequence of the genomic region to which each modified histone was bound was identified. In addition, ATAC-seq was also performed to identify the nucleotide sequence of the genomic region having an open chromatin structure.

Figure 4:
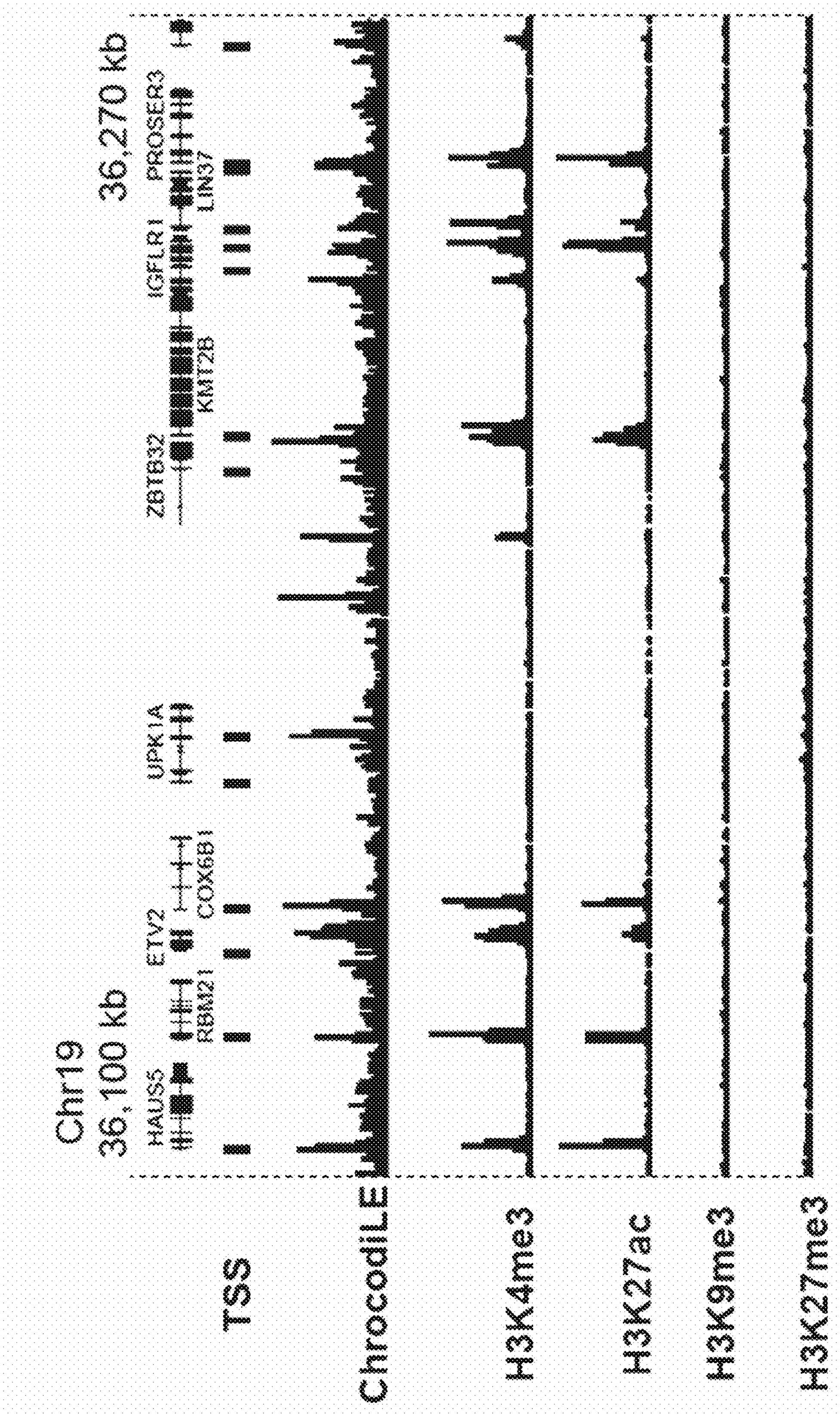
FIG. 4 shows a diagram showing the results of identifying the base sequence of the genomic region to which ChrocodiLE was bound in Example 2.

FIG. 4 shows the identified ChrocodiLE binding regions for the 36,100-36,270 kb region of chromosome 19 together with the transcription start sites (TSS). In addition, the genomic region having an open chromatin structure identified by ATAC-seq (top in the figure) and the genomic region to which four types of modified histones were bound are also shown. As a result, it was found that ChrocodiLE was bound to almost the same region as the region identified by ATAC-seq. In addition, Chrocode LE was also bound near the transcription initiation site of UPK1A, which was not identified by ATAC-seq. Since there is a high possibility that the vicinity of the transcription start site has an open chromatin structure, it was considered that ChrocodiLE recognizes the open chromatin structure, similar to ATAC-seq, and also recognizes the open chromatin structure that cannot be recognized by ATAC-seq. From these results, it was found that Chrocode LE is very useful as a probe for labeling the open chromatin structure.

Example 3

A transgenic mouse (hereinafter, may be referred to as "ChrocodiLE-Tg mouse") was prepared in which the gene encoding ChrocodiLE-EGFP, which was obtained by fusing the ChrocodiLe (protein having a DNA-binding domain in which 15 non-selective binding TAL-repeats are repeatedly linked) prepared in Example 1 with the fluorescent protein EGFP, was knocked in at the ROSA26 locus. ChrocodiLE-EGFP was prepared by linking a base sequence (SEQ ID NO: 4) encoding ChrocodiLE and a base sequence encoding EGFP. The transgenic mouse was prepared according to the method of Abe et al. (NPL 7).

Figure 5:
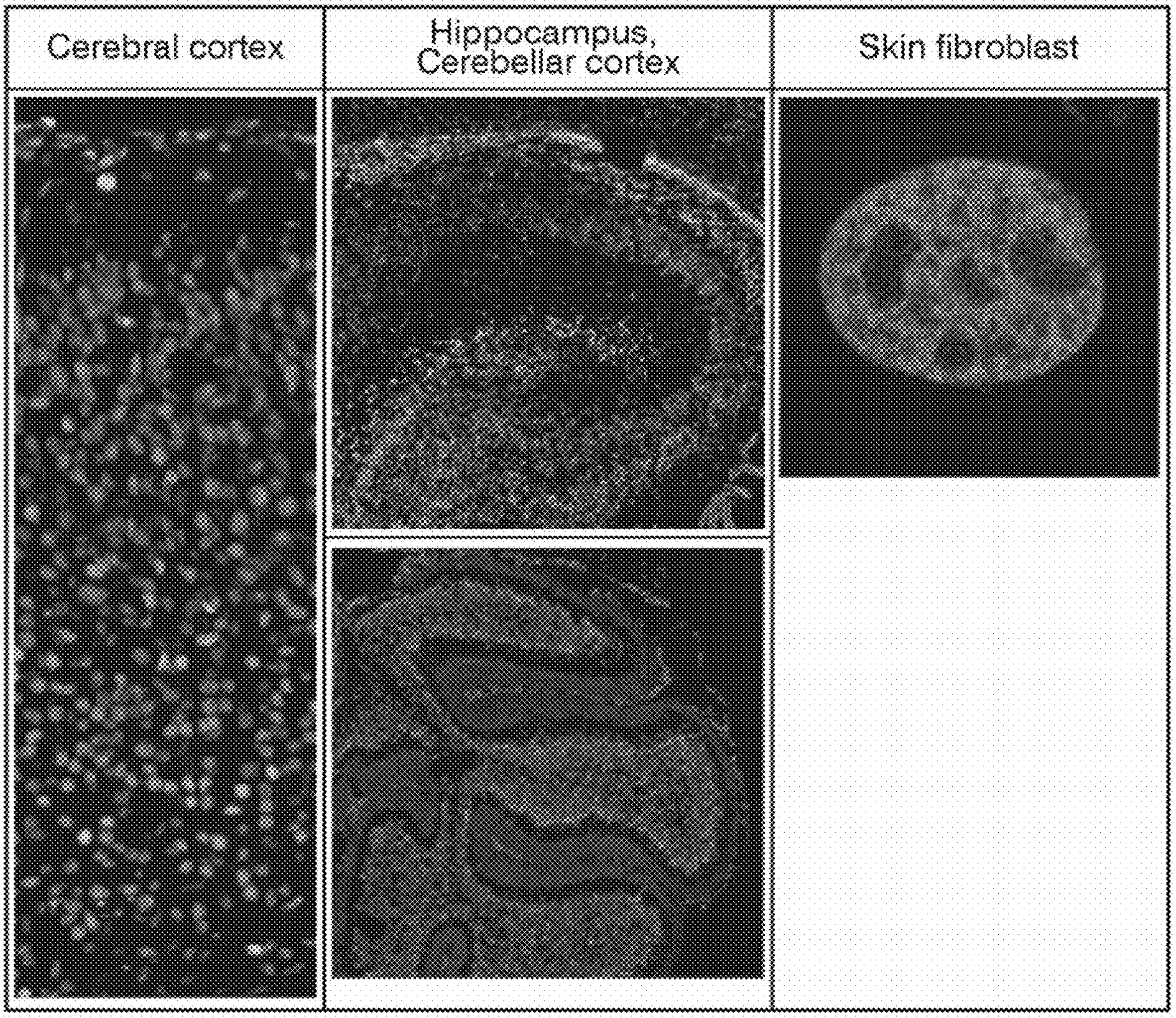
FIG. 5 shows a fluorescence image of thin sections of cerebral cortex, hippocampus, cerebellar cortex, and skin tissue of the ChrocodiLE-Tg mouse prepared in Example 3.

Thin-layer sections were prepared from each tissue of the prepared ChrocodiLE-Tg mice, and fluorescence images were acquired. Fluorescent images of the cerebral cortex, hippocampus and cerebellar cortex of the brain and a fluorescent image of the skin tissue are shown in FIG. 5. Expression of ChrocodiLE-EGFP was confirmed in all tissues.

Example 4

A transgenic nematode (hereinafter sometimes referred to as "ChrocodiLE-Tg nematodes") was prepared by inserting a gene encoding ChrocodiLE-GFP prepared by fusing the ChrocodiLe (protein having a DNA-binding domain in which 15 non-selective binding TAL-repeats are repeatedly linked) prepared in Example 1 with the fluorescent protein GFP. CrocodiLE-Tg nematodes were prepared by the MosSCI method. The expression vector was prepared by inserting a fragment between mex5 (promoter) derived from pJA252 (Plasmid #21512, manufactured by Addgene) and tbb2 (3'UTR) derived from pCM1.36 (Plasmid #17249) in pCFJ150-pDESTTTi5605 [R4-R3] (Plasmid #19329, manufactured by Addgene), the fragment being inserted with a gene encoding Chrocode LE-GFP inserted.

Figure 6:
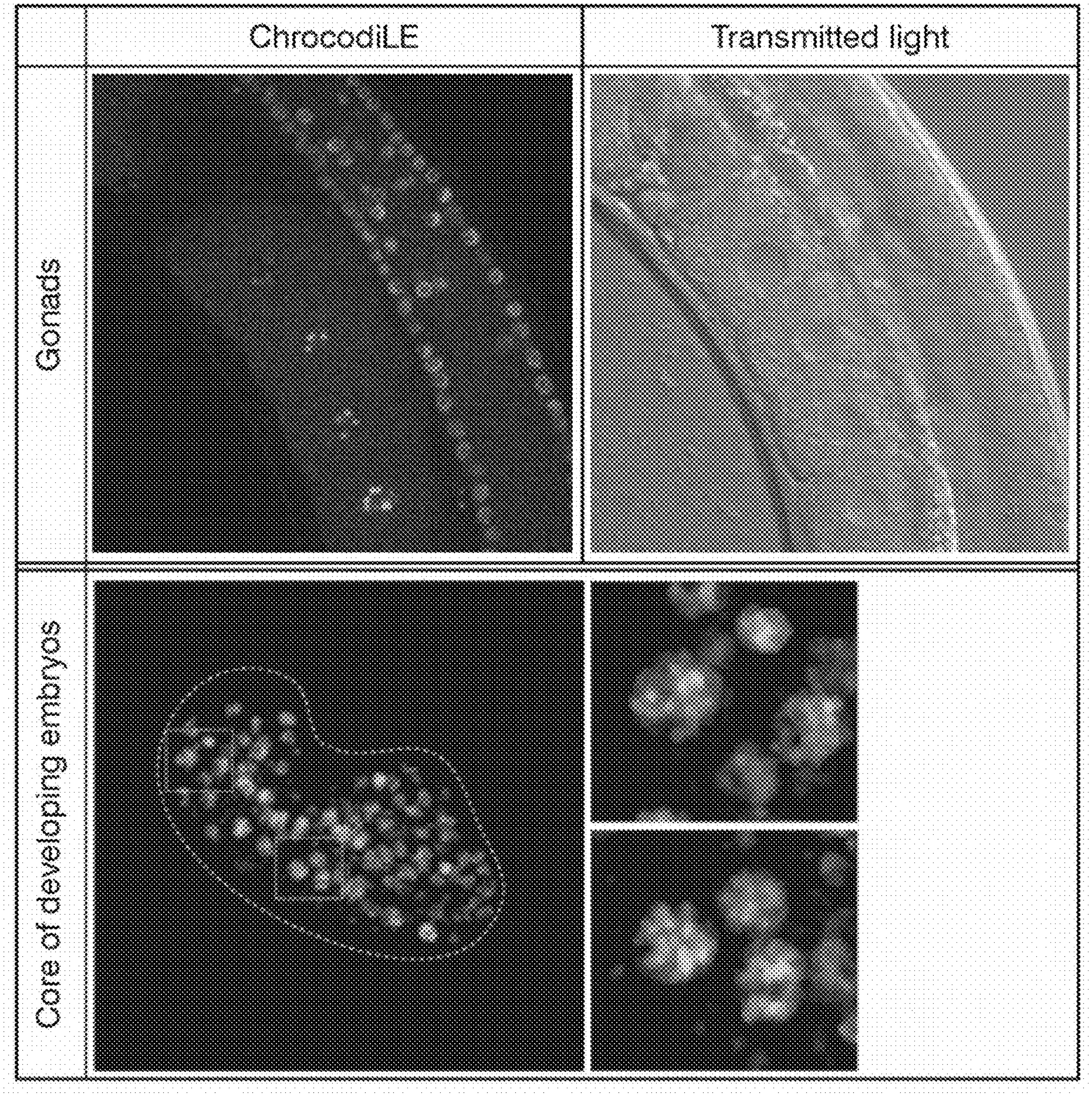
FIG. 6 shows a fluorescence image of thin sections of gonad and developing embryo of ChrocodiLE-Tg nematode prepared in Example 4.

Thin-layer sections were prepared from the gonads and developing embryos of the prepared ChrocodiLE-Tg nematodes, and fluorescence images were obtained. These fluorescent images are shown in FIG. 6. For the gonads, a transmitted light image of the same field of view is also shown. Of the fluorescence images of embryos, the right figure is an enlarged image of the left figure. Expression of ChrocodiLE-EGFP was also confirmed in the gonads and developing embryos.

INDUSTRIAL APPLICABILITY

The nucleic acid-binding protein according to the present invention strongly binds to nucleic acid in a base sequence-independent manner. Therefore, the nucleic acid-binding protein is useful as a probe that specifically recognizes the open chromatin structure, and is particularly useful for epigenome research in living cells. By using the nucleic acid-binding protein, it is possible to detect unknown gene activation sites and track the structural changes in chromatin over time in living cells, thereby providing an effective tool for clarifying the relationship between drug effects, diseases and epigenome changes.

What is claimed is:

1. A nucleic acid-binding protein comprising a DNA-binding domain, wherein the DNA-binding domain consists of 3 or more and less than 35 Transcription Activator-Like-repeats (TAL-repeats) that are repeatedly linked, and wherein the Repeat Variable Di-residue (RVD) sequences of the TAL-repeats in the DNA-binding domain consist of a sequence pair selected from the following groups: histidine-threonine, arginine-serine, histidine-serine, or a combination thereof.

2. The nucleic acid-binding protein according to claim 1, wherein all TAL repeats in the DNA binding domain consist of the same RVD sequence.

3. The nucleic acid-binding protein according to claim 1, wherein the TAL-repeats contained in the DNA-binding domain are TAL-repeats of TALE derived from a bacterium belonging to the genus *Xanthomonas*, or TAL-repeats in which an amino acid mutation is introduced in a region other than the RVD of the TAL-repeats.

4. The nucleic acid-binding protein according to claim 1, wherein the nucleic acid-binding protein further comprises a fluorescent protein, and the DNA-binding domain and the fluorescent protein are directly or indirectly bound to each other.

5. A protein probe comprising the nucleic acid-binding protein according to claim 1, which selectively binds to an open chromatin structure.

6. A nucleic acid molecule containing a nucleotide sequence encoding the nucleic acid-binding protein according to claim 1.

7. An expression vector comprising the nucleic acid molecule according to claim 6.

8. A method for fluorescently labeling open chromatin in living cells, comprising a step of introducing a gene encoding the nucleic acid-binding protein according to claim 4 into a living cell.

9. A transformed non-human cell comprising the nucleic acid molecule according to claim 6.

10. A transformed non-human animal comprising, in at least one cell of the non-human animal, the nucleic acid molecule according to claim 6.

11. The nucleic acid-binding protein according to claim 1, wherein the repetition number of the TAL-repeats in the DNA-binding domain is 3 or more and less than 15.

* * * * *